(12) United States Patent
Goldman

(10) Patent No.: US 8,722,349 B2
(45) Date of Patent: May 13, 2014

(54) METHODS AND KIT FOR ENDOMETRIOSIS SCREENING

(75) Inventor: Dorothee Goldman, Hammondsport, NY (US)

(73) Assignee: Oratel Diagnostics, LLC, Hammondsport, NY (US)

( * ) Notice: Subject to any disclaimer, the term of this patent is extended or adjusted under 35 U.S.C. 154(b) by 917 days.

(21) Appl. No.: 12/294,535

(22) PCT Filed: Mar. 29, 2007

(86) PCT No.: PCT/US2007/007803
§ 371 (c)(1),
(2), (4) Date: Jun. 11, 2010

(87) PCT Pub. No.: WO2007/126982
PCT Pub. Date: Nov. 8, 2007

(65) Prior Publication Data
US 2010/0267003 A1    Oct. 21, 2010

Related U.S. Application Data

(60) Provisional application No. 60/788,058, filed on Apr. 3, 2006, provisional application No. 60/875,527, filed on Dec. 19, 2006.

(51) Int. Cl.
*G01N 31/00* (2006.01)
*G01N 33/53* (2006.01)

(52) U.S. Cl.
USPC ........... 435/7.21; 435/7.1; 436/501; 436/518; 424/130.1; 424/9.1; 530/300; 530/350

(58) Field of Classification Search
CPC .......... A61K 38/00; A61K 39/00; B01L 9/00; C07K 14/705; C07K 16/18; G01N 33/582; G01N 33/6893
See application file for complete search history.

(56) References Cited

U.S. PATENT DOCUMENTS

| | | | |
|---|---|---|---|
| 4,358,288 A | 11/1982 | Goldman | |
| 5,334,502 A | 8/1994 | Sangha | |
| 5,356,817 A | 10/1994 | Cole | |
| 5,922,613 A | 7/1999 | Goldman | |
| 5,981,291 A | 11/1999 | Goldman | |
| 6,294,349 B1 | 9/2001 | Streckfus | |
| 6,531,277 B2 | 3/2003 | Timms | |
| 6,645,725 B2 | 11/2003 | Yeaman | |
| 6,780,594 B2 | 8/2004 | Hess-Stump et al. | |
| 6,867,051 B1 | 3/2005 | Anderson et al. | |
| 6,972,180 B1 | 12/2005 | Streckfus et al. | |
| 2003/0166014 A1 | 9/2003 | Timms | |
| 2005/0220912 A1 | 10/2005 | Theoharides | |
| 2005/0240085 A1 | 10/2005 | Knoell et al. | |
| 2006/0013905 A1 | 1/2006 | Tehoharides | |
| 2008/0200379 A1 | 8/2008 | Tabibzadeh et al. | |
| 2008/0241852 A1 | 10/2008 | Messer et al. | |
| 2010/0272637 A1 | 10/2010 | Schilling | |
| 2011/0015087 A1 | 1/2011 | Nagore Casas et al. | |

FOREIGN PATENT DOCUMENTS

| WO | WO 9629606 A | 9/1996 |
|---|---|---|
| WO | WO 0047739 A | 8/2000 |
| WO | 2007/126982 A1 | 11/2007 |

OTHER PUBLICATIONS

Attia et al. (The Journal of Clinical Endocrinology and Metabolism, 2000, vol. 85, No. 8, pp. 2897-2902).*
Goldman (Mar. 20, 2006).*
International Search Report, International Application No. PCT/US2012/046175, mailed Oct. 5, 2012, 4pp.
"Saliva may paint an insightful view of the body's health." Medilexicon. Jun. 12, 2005. http://www.medilexicon.com/medicalnews.php?newsid=26004.
Dorothee Goldman. "A discussion about pH patterns and absorbency patterns for malividin 3,5 digluocside mixed with saliva samples from a woman with endometriosis and a woman who does not have endometriosis and a comparison of estradiol levels in saliva to pH patterns and to optical density patterns." Mar. 20, 2006.
S. Simoens et al, "Endometriosis: cost estimates and methodological perspective", Hum Reprod Update, 2007, pp. 395-404 vol. 13 No. 4.
T. Price et al, "Immunofluorescent Localization of a Novel Progesterone Receptor(s) in a T47D-Y Breast Cancer Cell Line Lacking Genomic Progesterone Receptor Expression", J Soc Gynecol Investig, Dec. 2005, pp. 610-616, vol. 12, No. 8.
B. Kay et al, "The importance of being proline: the interaction of proline-rich motifs in signaling proteins with their cognate domains", The FASEB Journal, Feb. 2000, pp. 231-241, vol. 14.
V. Boonyaratanakornkit et al, "Progesterone Receptor Contains a Proline-Rich Motif that Directly Interacts with SH3 Domains and Activates c-Src Family Tyrosine Kinases", Molecular Cell, Aug. 2001, pp. 269-280, vol. 8.

(Continued)

*Primary Examiner* — Lisa Cook
(74) *Attorney, Agent, or Firm* — Berenato & White, LLC

(57) ABSTRACT

Methods of screening a bodily sample for endometriosis are provided. The bodily sample is preferably saliva. According to one embodied method, the bodily sample is subjected to a denaturing procedure, and a property of the bodily sample observed after the denaturing procedure is evaluated for the presence or absence of a factor correlating to endometriosis as part of an endometriosis screening procedure. The methods embodied herein are preferably conducted in combinations which permit for the evaluation of at least two different physiological factors correlating to endometriosis, because women with endometriosis do not always share the same factors. Also provided are screening kits, assay methods, and systems for endometriosis screening.

15 Claims, 14 Drawing Sheets

(56) References Cited

OTHER PUBLICATIONS

G. Proctor et al, "The Function of Salivary Proteins and the Regulation of Their Secretion by Salivary Glands", Biomedical Reviews, 1998, pp. 3-15, vol. 9.

P.G. Groothuis et al, "Estrogen and the endometrium: lessons learned from gene expression profiling in rodents and human", Human Reproduction Update, 2007, pp. 405-417, vol. 13 No. 4.

K. Pettersson et al, "Role of Estrogen Receptor Beta in Estrogen Action", Annual Review of Physiology, 2001, pp. 165-192, vol. 63.

P. Calias et al, "Synthesis of inositol 2-phosphate-quercetin conjugates", Carbohydrate Research, 1996, pp. 83-90, vol. 292.

E. Markou et al, "The Influence of Sex Steroid Hormones on Gingiva of Women", The Open Dentistry Journal, 2009, pp. 114-119, vol. 3.

G. Attia et al, "Progesterone Receptor Isoform A But Not B Is Expressed in Endometriosis", The Journal of Clinical Endocrinology & Metabolism, 2000, pp. 2897-2902, vol. 85, No. 8.

J. Aplin, "MUC-1 glycosylation in endometrium: possible roles of the apical glycocalyx at implantation", Human Reproduction, 1999, pp. 17-25, vol. 14 (Suppl. 2).

S. Hild-Petito et al, "Mucin (Muc-1) Expression Is Differentially Regulated in Uterine Luminal and Glandular Epithelia of the Baboon (*Papio anubis*)"; Biology of Reproduction, 1996, pp. 939-947, vol. 54.

P. Sarni-Manchado et al, "Influence of the Glycosylation of Human Salivary Proline-Rich Proteins on Their Interactions with Condensed Tannins" Journal of Agricultural and Food Chemistry, 2008, pp. 9563-9569, vol. 56.

A. Rodgers et al, "Inhibition of CD44 N- and O-linked Glycosylation Decreases Endometrial Cell Lines Attachment to Peritoneal Mesothelial Cells", Fertil Steril., Feb. 2011, pp. 823-825, vol. 95, No. 2.

A. Van Nieuw Amerongen et al, "Salivary Proteins: Protective and Diagnostic Value in Cariology?", Caries Research, 2004, pp. 247-253, vol. 38.

G.B. Proctor et al, "Salivary Proteins Interact with Dietary Constituents to Modulate Tooth Staining", Journal of Dental Research, 2005, pp. 73-78, vol. 84, No. 1.

H. Zhang et al, "Use of proteomic analysis of endometriosis to identify different protein expression in patients with endometriosis versus normal controls", Fertility and Sterility, Aug. 2006, pp. 274-282, vol. 86, No. 2.

L. Margarit et al, "MUC1 as a Discriminator between Endometrium from Fertile and Infertile Patients with PCOS and Endometriosis", J Clin Endocrinol Metab, Dec. 2010, pp. 5320-5329, vol. 95 No. 12.

A. Bennick et al, "The Nature of the Hydroxyapatite-Binding Site in Salivary Acidic Proline-Rich Proteins", Biochem. J., 1979, pp. 115-126, vol. 183.

G. Madapallimattam et al, "Phosphopeptides derived from human salivary acidic proline-rich proteins", Biochem. J., 1990, pp. 297-304, vol. 270.

B. Sengupta et al, "The interaction of quercetin with human serum albumin: a fluorescence spectroscopic study", Biochemical and Biophysical Research Communications, 2002, pp. 400-403, vol. 299.

C. Dufour et al, "Flavonoid-serum albumin complexation: determination of binding constants and bindling sites by fluorescence spectroscopy", Biochemical and biophysical research communications, 2002, vol. 299 No. 3, 1 page Abstract.

B. Delvoux et al, "Increased Production of 17 beta-estradiol in Endometriosis Lesions Is the Result of Impaired Metabolism", J Clin Endocrinol Metab., Mar. 2009, pp. 876-883, vol. 94 No. 3.

M. Meseguer et al, "MUC1 and endometrial receptivity", Molecular Human Reproduction, 1998, pp. 1089-1098, vol. 4 No. 12.

Byoung-Moo Seo et al, "Investigation of multipotent postnatal stem cells from human periodontal ligament", The Lancet, Jul. 10, 2004, vol. 364, Issue 9429, 2 pp Summary.

H. Taylor, "Endometrial cells derived from donor stem cells in bone marrow transplant recipients", JAMA, 2004, pp. 81-85, vol. 292 No. 1, 2 pp Abstract.

K. Sakabe et al, "Progestin and estrogen receptors: characterization and localization in rat submandibular glands, with special reference to epidermal growth factor", Endocrinol Jpn., Oct. 1988, vol. 35, No. 5, 1 pg. Abstract.

A. Zalewska et al, "Structure and biosynthesis of human salivary mucins", Acta Biochimica Polonica, 2000, pp. 1067-1079, vol. 47 No. 4.

Gargett, "Uterine stem cells: What is the evidence?", Human Reproduction Update, 2007, pp. 87-101, vol. 13, No. 1.

J. Ai et al, "Endometrial Stem Cells and Endometriosis", http://www.intechopen.com/books/endometriosis-basic-concepts-and-current-research-trends/endometrial-stem-cells-and-endometriosis, pp. 297-308, May 9, 2012.

Lori et al, "Mechanism for the Adsorption of Mucin on Hydroxyapatite", Nigerian Journal of Chemical Research, 2005, pp. 21-29, vol. 10.

A. Fukushima et al, "Role of Na+ and Ca2+ Channels in the Preoptic LH Surge Generating Mechanism in Proestrous Rats", Endocrine Journal, 2003, pp. 145-153, vol. 50 No. 2.

V. Braga et al, "Modulation of Muc-1 mucin expression in the mouse uterus during the estrus cycle, early pregnancy and placentation", Journal of Cell Science, 1993, pp. 397-405, vol. 105.

B, Madhan et al, "A Semi-Empirical Quantum Mechanical Modeling Study on the Interaction of Collagen-like Peptides with Polyphenolic Molecules: An Attempt to Gain Insights into Vegetable Tanning", JALCA, 2003, pp. 272-277, vol. 98.

S. Chiappin et al., "Saliva specimen: A new laboratory tool for diagnostic and basic investigation", Clinica Chimica Acta 383, 2007, pp. 30-40.

H. Valimaa et al, "Estrogen receptor-beta is the predominant estrogen receptor subtype in human oral epithelium and salivary glands", Journal of Endocrinology, 2004, pp. 55-62, vol. 180.

Ja-Mun Chong et al, "Interleukin 1beta Expression in Human Gastric Carcinoma with Epstein-Barr Virus Infections", Journal of Virology, Jul. 2002, pp. 6825-6831, vol. 76 No. 13.

C. Ballare et al, "Two Domains of the Progesterone Receptor Interact with the Estrogen Receptor and Are Required for Progesterone Activation of the c-Src/Erk Pathway in Mammalian Cells", Molecular and Cellular Biology, Mar. 2003, pp. 1994-2008, vol. 23 No. 6.

M.E. Baker, "Beyond Carrier Proteins Albumin, steroid hormones and the origin of vertebrates", Journal of Endocrinology, 2002, pp. 121-127, vol. 175.

S. Kavoussi et al, "Periodontal disesase and endometriosis: Analysis of the National Health and Nutrition Examination Survey", Fertility and Sterilility, Feb. 2009, pp. 335-342; vol. 91 No. 2.

J. Hu et al, "Carbonic Anhydrase Regulate Endometrial Gland Development in the Neonatal Uterus", Biology of Reproduction, 2005, pp. 131-138; vol. 73.

D. He et al, "Characterization of Proline-Serine-Rich Carboxyl Terminus in Human Sulfotransferase 2B1b: Immunogenicity, Subcellular Localization, Kinetic Properties, and Phosphorylation", Drug Metabolism and Disposition, pp. 1749-1755, vol. 34 No. 10, 2006.

M. C. Rose et al, "Respiratory Tract Mucin Genes and Mucin Glycoproteins in Health and Disease", Physiological Reviews, 2006, pp. 245-278, vol. 86.

G. Goobes et al, "Folding of the C-terminal bacterial binding domain in statherin upon adsorption onto hydroxyapatite crystals", PNAS, Oct. 31, 2006, pp. 16083-16088, vol. 103 No. 44.

N. Heldring et al, "Estrogen Receptors: How Do They Signal and What Are Their Targets", Physiological Reviews, 2007, pp. 905-931, vol. 87.

E. Azen et al, "Genetic Polymorphism of Proline-Rich Human Salivary Proteins", Science, Jun. 8, 1973, pp. 1067-1069; vol. 180 No. 4090, 1 page Abstract.

S. Senapati et al, "Mucin-interacting proteins: from function to therapeutics", Trends in Biochemical Sciences, Apr. 2010, pp. 236-245, vol. 35 No. 4.

International Search Report, International Application No. PCT/US2007/007803, mailed Jun. 9, 2007, 4pp.

International Search Report, International Application No. PCT/US11/46586, mailed Mar. 8, 2012, 4pp.

(56) References Cited

OTHER PUBLICATIONS

Bedaiwy M A et al, "Prediction of endometriosis with serum and peritoneal fluid markers: a prospective controleed trial," Human Reproduction, Feb. 2002, pp. 426-431 vol. 17, No. 2, IRL Press, Oxford, GB, 2002.

Koshiba Hisato et al, "Expression of allograft inflammatory factor-1 in human eutopic endometrium and endometriosis: Possible association with progression of endometriosis" Journal of Clinical Endocrinology & Metabolism, Jan. 2005, pp. 529-537, vol. 90, No. 1, 2005.

E. Attar et al., Aromatase and other steroidogenic genes in endometriosis: translational aspects; Human Reproduction Update, vol. 12, No. 1, 49-56 (2005).

H. Valimaa, et al., Estrogen receptor-beta is the predominant estrogen receptor subtype in human . . . salivary glands; Journal of Endocrinology; vol. 180, 55-62 (2004).

T. Ediger, et al., Estrogen Receptor Regulation of the Na+/H+ Exchanger Regulatory Factor, Endocrinology, vol. 140, No. 7, 2976-2982 (1999).

Sevon et al., Effect of Age on Flow-Rate, Protein and Electrolyte Composition of Stimulated Whole Saliva in Healthy, Non-Smoking Women, Open Dent J.; 2: 89-92 (2008).

L.C. Kao, et al, Expression Profiling of Endometrium for Women with Endometriosis Reveals Candidate . . . and Infertility; Endocrinology, vol. 144, No. 7; 2870-2881 (2003).

Parkkila, et al., Immunohistochemical localization of carbonic anhydrase isoenzymes VI, II, and I . . . glands, J. of Histochemistry and Cytochemistry, 38(7) 941 1990 (abstract).

E. Szmuilowicz, et al., Relationship between Aldosterone and Progesterone in Human Menstrual Cycle, J. of Clinical Endocrinology & Metabolism, vol. 91, No. 10, 3981-3987 (2006.

Clemetson, et al., The Effects of Oestrogen and Progesterone on the Sodium and Potassium Concentrations of Rat Uterine Fluid, J. of Endocrinology, 47 (1970 (abstract).

S. Bulun, Endometriosis, vol. 360, No. 3, 268-279 (2009).

Research Projects: Theory and Modelling (6 pages), Dec. 29, 2009.

C. Hannig, et al., Transaminases in the acquired pellicle, Archives of Oral Biology, vol. 54, No. 5, May 2009 (abstract).

Giovanna Fia, et al., Prediction of grape polyphenol astringency by means of a fluorimetric micro-plate assay, Food Chemistry, vol. 113, No. 1 (2009) (abstract).

R.M. Nagler, Salivary glands and the aging process: mechanistic aspects, health-status and medicinal-efficacy monitoring, Biogerontology 5: 223 (2004).

G.R. Attia, Progesterone Receptor Isoform A But Not B is Expressed in Endometriosis, J. of Clinical Endocrinology & Metabolism, vol. 85, No. 8, 2897-2902 (2000).

N.S. Stachenfeld, Progesterone increases plasma volume independent of estradiol, J. Applied Physiol., 98: 1991-1997 (2005).

G.B. Proctor, et al., Salivary Proteins Interact with Dietary Constituents to Modulate Tooth Staining, J. Dent. Res. 84(1): 73-78 (2005).

\* cited by examiner

Fig. 6
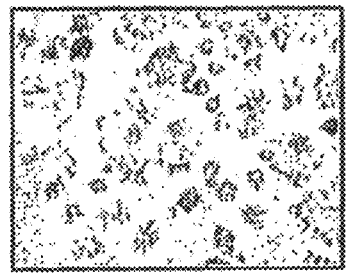

Fig. 7
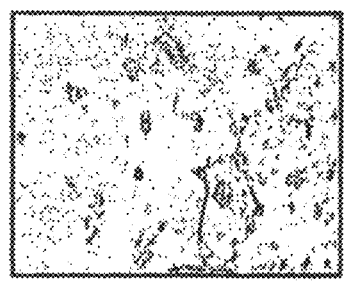
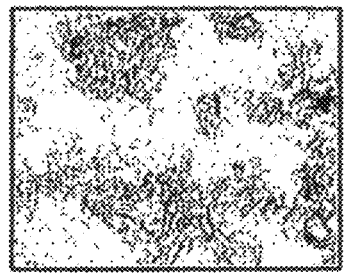
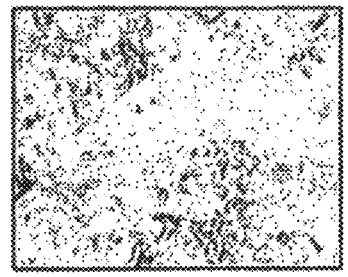

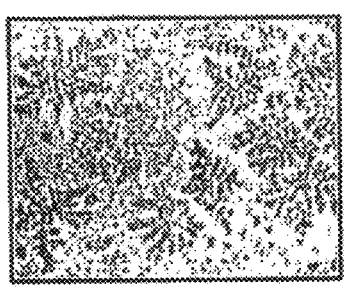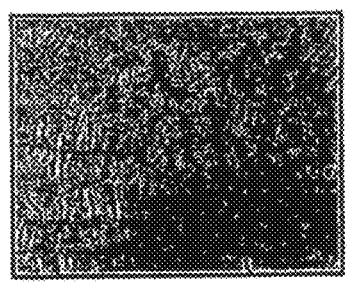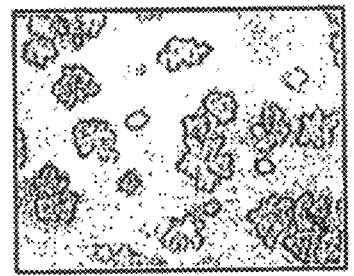
Fig. 8

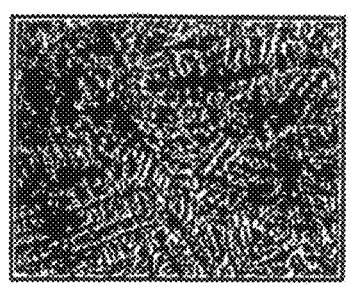
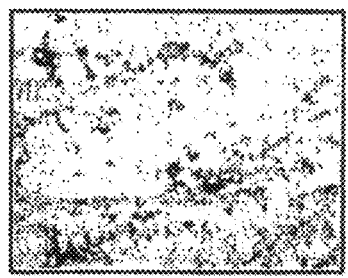
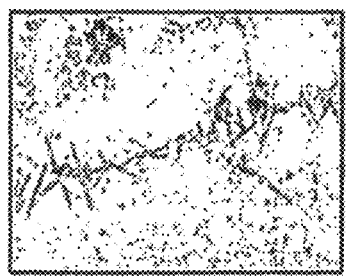
Fig. 10

Fig. 11
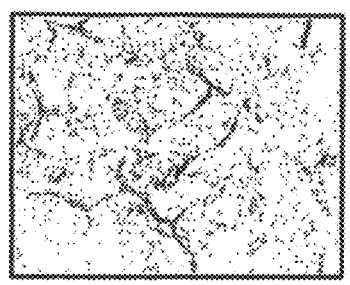
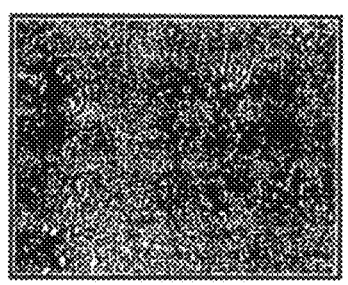
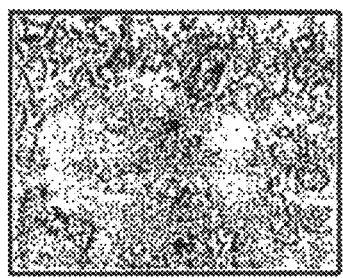

Absorbency for mv3,5 gg mixed with saliva

Absorbency for mv3,5 gg mixed with saliva

Absorbency for mv3,5 gg mixed with saliva

Absorbency values for 1x10-4 molar mvgg mixed with saliva

METHODS AND KIT FOR ENDOMETRIOSIS SCREENING

CROSS-REFERENCE TO RELATED APPLICATIONS AND CLAIM TO PRIORITY

This application is a National Phase of International Application No. PCT/US2007/07803 filed Mar. 29, 2007 and claims benefit of priority to provisional application No. 60/788,058 filed on Apr. 3, 2006 and provisional application No. 60/875,527 filed on Dec. 19, 2006.

FIELD OF THE INVENTION

The present invention is directed to improved and reliable systems, methods and kits for detecting one or more physiological factors expressed in a bodily sample, such as saliva, as part of an endometriosis screening evaluation. In preferred embodiments of the invention, the bodily sample is obtained in a non-invasive manner, and the systems, methods, and kits allow for early and reliable identification of endometriosis.

BACKGROUND OF THE INVENTION

Endometriosis has been classified as an immune deficiency disease ("Pathogenesis of Endometriosis: Natural Immunity Dysfunction or Autoimmune Disease," *Trends Mol. Med.*, 9(5):223-8, May 2003, G. Matarase, G. De Placido, Y. Nikas, C. Alviggi) that affects about 7 percent of the pre-menopausal women worldwide in their reproductive years. Endometriosis is characterized by ectopic lesions of endometrial tissue in various organs of the body outside the uterus. *Harvard Medical School Family Health Guide*, p. 1071, 1999, A. Komaroff. Ectopic lesions of endometrial tissue are often found on the ovaries, fallopian tubes, ligaments that support the uterus, areas around the vagina and uterus, areas within the pelvic cavity, and combinations of these areas. Other sites of ectopic lesions may include the vagina, cervix, vulva, bladder, and bowel, as well as other areas. The ectopic lesions form benign tumors on organs when there is an immune deficiency in the patient.

The ectopic endometrial lesions characteristic of endometriosis are similar to endometrial tissue which lines the uterus. Unlike endometrial tissue lining the uterus, however, ectopic endometrial lesions are unable to discharge from the body during menstruation. Internal bleeding results from the ectopic endometrial lesions, leading to the development of inflammation and scar tissue. The ectopic endometrial lesions have also been reported to generate blood vessels by a process known as angiogenesis. The ectopic endometrial lesions can also develop nerve tissue, which enhances sensitivity to inflammation.

Several theories exist with regard to the etiology and pathogenesis of endometriosis and the growth of the ectopic lesions. It is generally accepted that endometrial cells and fragments desquamate during the menstrual period and are transported through the fallopian tubes. The endometrial cells and fragments are implanted, proliferate, and develop outside the uterus, such as in the peritoneal cavity. Studies have suggested that alterations in the immune response of a woman predispose her to the ectopic implants of endometrial cells. *New considerations for the pathogenesis of endometriosis*, Int. J. Gynaecol Obstet, 2002 February; 76(2):117-26, Gazavani, R, Templeton, A.

There are many factors involved in the pathogenesis of endometriosis that vary considerably within the population of females having endometriosis. *Endometriosis, The Complete Reference for Taking Charge of Your Health, Contemporary Books*, p. 175, 2003, M. Ballweg. These different factors manifest in different manners, resulting in a likewise high variation of symptoms within the relevant female population. For example, one of the symptoms of endometriosis is infertility. While endometriosis is one of the leading causes of infertility in women, it is estimated that about 30 to 40 percent—less than half—of women with endometriosis suffer from fertility problems. Similarly, while the above-discussed increased sensitivity brought about by inflammation, scar tissue, and nerve tissue growth manifests as discomfort or severe pain, not all women afflicted with endometriosis experience the severe pain, and oftentimes severe pain can be attributed to another cause. Other symptoms of endometriosis may include inflammation, chronic pain, diarrhea, intestinal pain, painful intercourse, abdominal tenderness, cramping, back ache, menstrual cramps, excessive menstrual bleeding, and pelvic pain. However, linking these symptoms to an endometriosis diagnosis is extremely difficult. These symptoms are not universally experienced throughout the population of females having endometriosis. Further, these symptoms can be brought about by other illnesses.

The wide variety of symptoms exhibited by females having endometriosis, combined with the other possible explanations and diagnoses for the symptoms, imparts a large degree of uncertainty to endometriosis diagnoses. Using conventional models, it may take many years and/or many repeated tests before a practitioner can confidently verify whether or not a woman has endometriosis. *Endometriosis, The Complete Reference for Taking Charge of Your Health, Contemporary Books*, p. 354-357, 2003, M. Ballweg.

Accordingly, there is a need in the art for an endometriosis screening system, kit, and method that are able to overcome the difficulties and uncertainties inherent to conventional symptom diagnoses. The system, kit, and method preferably are non-invasive in application to promote regular testing and to remove the fear associated with invasive methods, thereby encouraging repeated and periodic testing and early stage intervention.

SUMMARY OF THE INVENTION

In accordance with the principles of the invention as embodied and described herein, a first aspect of the invention provides a method of screening for endometriosis in a female subject, comprising collecting at least one sample (specimen) from the female subject, performing a first assay on the sample to evaluate for a first physiological factor, the presence or absence of which correlates to endometriosis, performing a second assay on the sample to evaluate for a second physiological factor, the presence or absence of which correlates to endometriosis, the first and second physiological factors differing from one another, and evaluating whether the female subject has endometriosis based on the presence or absence of the physiological factors.

Many (but not necessary all) of the aspects and embodiments of the present invention, including the first aspect described above and assay methods and assay kits described below, operate under the premise that there are multiple different physiological factors associated with the pathogenesis of endometriosis, and that these factors are not all shared universally with females afflicted with endometriosis. As will be explained in greater detail below, and without wishing to be bound by any theory, some of these factors are sensitive to estrogen metabolism imbalances, while other factors are due to immune responses with or without inflammation responses. By concurrently testing for a plurality of these physiological factors, the reliability and accuracy of the diagnosis can be increased because female subjects lacking certain physiological factors will not be overlooked by a test that focuses on only one physiological factor. Beneficially, the likelihood of early detection is greatly improved, and the diagnosed subject can receive timely treatment for the particular form of endometriosis from which she may be suffering before it progresses too far.

Aspects of the present invention also relate to individual endometriosis screening methods, assay methods, and assay kits that may be implemented as part of the method of the first aspect described above, or which may be implemented in other manners, e.g., as an individual screening system, assay method, or kit.

A second aspect of the invention provides a method of screening for endometriosis in a female subject, comprising subjecting a bodily sample to a denaturing procedure, and evaluating a property of the bodily sample after the denaturing procedure as part of a endometriosis screening procedure.

In an embodiment of this second aspect of the invention, the denaturing procedure comprises subjecting the bodily fluid to at least one freezing and thawing cycle. In accordance with another embodiment of this second aspect of the invention, the measured property is pH, and the evaluating comprises determining the difference in the property measured before and after the denaturing procedure. In another embodiment of this second aspect, the property comprises crystalline formations of the dehydrated bodily fluid. Optionally, as part of the evaluation the crystalline formations are compared to reference microphotographs.

A third inventive aspect provides a method of screening for presence of endometriosis in a female subject, comprising providing a mixture comprising a bodily sample and a flavonoid pigment (such as quercetin or an anthocyanin), measuring first and second optical density values of the mixture at first and second wavelengths, respectively, calculating a mathematical relationship value between the first and second optical density values in order to evaluate the "slope" or rate of change in absorbency value between any two wavelengths, and comparing this mathematical relationship or slope value to a reference scale as part of an endometriosis screening procedure.

A fourth aspect of the invention provides a method of screening for endometriosis in a female subject, comprising combining a bodily fluid sample mixed with a flavonoid pigment, preferably yet optionally quercetin, treating the sample with an indicator or reagent, preferably diluted tincture of iodine, and evaluating a color response as part of an endometriosis screening procedure.

A fifth aspect of the invention provides a method for the detection of endometriosis in a female subject, comprising subjecting a bodily sample to a filtering procedure, measuring a property of the bodily sample prior and subsequent to the filtering procedure, and evaluating the measured property as part of an endometriosis screening procedure. In an embodiment of this fifth aspect of the invention, the bodily sample is combined with a color response system, such as a pigment, and the first and second measured properties are color observations which are compared to one another in order to determine whether filtering caused a color change to the treated bodily fluid sample.

A sixth aspect of the invention provides a method of screening for endometriosis in a female subject, comprising combining a bodily fluid sample with quercetin, subjecting the bodily fluid sample to a chromatography procedure, and evaluating results of the chromatography procedure as part of an endometriosis screening procedure.

A seventh aspect of the invention provides an assay method comprising performing a first assay on a first non-invasive bodily sample; evaluating the first assay for a first physiological factor, the presence or absence of which in the first non-invasive bodily sample correlates to endometriosis; performing a second assay on a second non-invasive bodily sample; and evaluating the second assay for a second physiological factor, the presence or absence of which in the second non-invasive bodily sample correlates to endometriosis, the first and second physiological factors differing from one another.

An assay method according to an eighth aspect of the invention comprises performing a denaturing assay on a non-invasive bodily sample, and evaluating a property of the bodily sample after the denaturing assay. In a preferred embodiment of this aspect, the denaturing assay comprises at least one freezing and thawing cycle, and first and second pH measurements of the non-invasive bodily sample are respectively taken before and after the freezing and thawing cycle. In another preferred embodiment of this aspect, the denaturing assay comprises dehydrating the bodily sample, and crystalline formations of the dehydrated bodily sample are evaluated. According to another preferred embodiment of this eighth aspect, the assay method comprises combining the bodily sample with a flavonoid pigment, measuring first and second optical density values of the combination of the bodily sample and the flavonoid pigment at first and second wavelengths, respectively, prior to the denaturing assay, measuring first and second optical density values of the combination of the bodily sample and the flavonoid pigment at first and second wavelengths, respectively, subsequent to the denaturing assay, and comparing the optical density values prior and subsequent to the denaturing assay.

A ninth aspect of the invention resides in an assay method, comprising measuring first and second optical density values of a mixture comprising a bodily sample and a flavonoid pigment at first and second wavelengths, respectively, and calculating a mathematical relationship value between the optical density values.

An assay method according to a tenth aspect of the invention comprises combining a non-invasive bodily sample with a quercetin pigment,
   treating the sample and the quercetin pigment with diluted tincture of iodine and detecting for a color response, and
   evaluating the color response.

An eleventh aspect of the invention provides an assay method comprising combining a non-invasive bodily fluid sample with quercetin, subjecting the bodily fluid sample to a chromatography procedure, and evaluating results of the chromatography procedure.

A twelfth aspect of the invention provides a kit comprising a platform for receiving bodily samples and carrying out a first assay on a first non-invasive bodily sample to evaluate for a first physiological factor correlating to endometriosis and a second assay on a second non-invasive bodily sample to evaluate for a second physiological factor correlating to endometriosis, the first and second physiological factors differing from one another.

Other aspects of the invention reside in kits for carrying out the methods and assay methods of the first to twelfth aspects of the invention.

BRIEF DESCRIPTION OF THE DRAWINGS

The accompanying drawings are incorporated in and constitute a part of the specification. The drawings, together with the general description given above and the detailed description of the preferred embodiments and methods given below, serve to explain the principles of the invention. In such drawings:

FIG. 6 are reference photographs taken at 200× magnification of saliva crystals observed in samples from women with endometriosis in the follicular phase;

FIG. 7 are reference photographs taken at 200× magnification of saliva crystals observed in samples from women without endometriosis in the follicular phase;

FIG. 8 are reference photographs taken at 200× magnification of saliva crystals observed in samples from women with endometriosis in the fertile phase;

FIG. 10 are reference photographs taken at 200× magnification of saliva crystals observed in samples from women with endometriosis in the luteal phase;

FIG. 11 are reference photographs taken at 200× magnification of saliva crystals observed in samples from women without endometriosis in the luteal phase;

Figure 1:
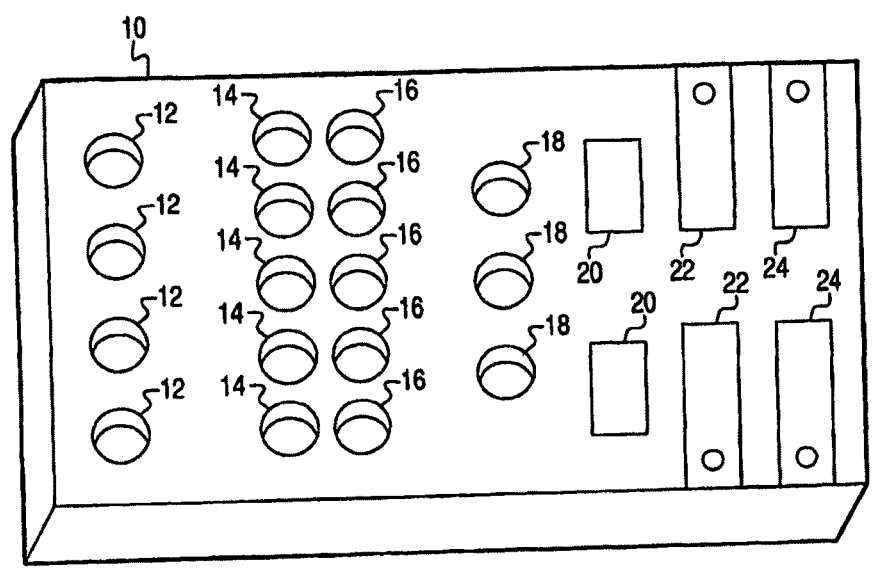
FIG. 1 is a perspective view of a kit for the screening of endometriosis according to an embodiment of the invention.

DETAILED DESCRIPTION OF THE PREFERRED
EMBODIMENTS AND PREFERRED METHODS
OF THE INVENTION

Reference will now be made in detail to the presently preferred embodiments and methods of the invention as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the preferred embodiments and methods. The invention according to its various aspects is particularly pointed out and distinctly claimed in the attached claims read in view of this specification, and appropriate equivalents.

The methods and systems described herein provide for the screening of endometriosis by making use of a bodily sample which possesses physiological factors that allow for the detection and screening of endometriosis. In particularly preferred embodiments of the invention, multiple testing procedures or methods are carried out in vitro on the bodily sample or plurality of samples to detect for the presence or absence of multiple physiological factors. Subjects of the population having endometriosis randomly differ from one another in the particular factors they possess. Measuring for multiple different factors increases the likelihood that at least one of the physiological factors possessed by an individual having endometriosis will be detected.

The selected bodily sample preferably yet optionally is considered a non-invasive medium that is attainable from the subject without requiring penetration of the skin, such as with a needle or scalpel as part of a surgical procedure. Preferably saliva is selected as the non-invasive bodily sample. Saliva is known to contain some of the same physiological factors found in serum, in concentrations that are linearly proportional to the concentrations measured in serum. ("Human Saliva as a Diagnostic Specimen", *Journal of Nutrition,* 131: 1621 S-1625S, 2001, L. Hofman) Further, saliva includes factors that respond to inflammation resulting from ectopic lesions. While saliva is preferred for use with the kits and systems of the invention and in practice of the methods of the invention, other bodily fluids and matter, such as epithelial cells, blood, sweat, or fluids from epithelial cells, etc., possessing factors that allow for like testing procedures to be carried out may be selected.

As will be discussed in further detail below, embodiments of the invention comprise endometriosis detection kits, systems, and methods for the detection of one or more physiological factors which are detectable in a bodily sample and correlate to endometriosis.

As noted above, inflammation is a symptom common in many but not all women afflicted with endometriosis. Endometrial inflammation is accompanied by an increase in concentration of certain factors, which presumably cause the inflammation and/or arise in response to the inflammation. In either case, saliva is an example of a bodily fluid rich in factors correlating to endometrial inflammation. Cytokines such as interleukin-6 have been recognized as potential markers for endometriosis. ("Prediction of Endometriosis With Serum and Peritoneal Fluid Markers," Human Reproduction," *Human Reproduction,* 17(2):426-31 ISSN: 0268-1161, 2002 Febuary, M. A. Bedaiwy, T. Falcone; R. K. Sharma, J. M. Goldberg, M. Attaran, Nelson) Cytokines have been implicated in the implantation and the growth of endometrial cells outside the uterus, as well as the development of inflammation. The concentration of cytokines increases in women with endometrial inflammation. (*ScienTotal Environment,* 65:85-94 1987, Hojo) (See also "Interleukin-6 (IL-6), an inflammatory cytokine is expressed abnormally in women with endometriosis" *J. of Clinical Endocrinology & Metabolism,* Vol. 90, No. 1, 529-537, 2005, Koshiba, et al.)

Peroxidases are another physiological factor found in increased levels in women with endometrial inflammation. Selenium glutathione peroxidase is also related to inflammatory responses and is present in human saliva and other human body fluids. Other peroxidases and lysomes also increase in both serum and saliva of women with endometriosis.

Certain flavonoids are particularly useful for enabling the detection of factors correlating to inflammation. A discussion of the relationship between the flavonoid quercetin and inflammation is found in "Luteolin Inhibits an Endotoxin-Stimulated Phosphorylation Cascade and Proinflammatory Cytokine Production in Macrophages," *Pharmacology: Therapeutics,* Vol. 296, Issue 1, 181-187, January 2001, A. Xagorari, A. Papapetropoulos, A. Mauromatis, M. Economou, T. Fotsis and C. Roussos. As will be described in greater detail below, quercetin can be used as a marker for certain of these peroxidases.

Physiological factors associated with immune responses and found in saliva also may serve as the subject of an endometriosis detection procedure. Certain prosthetic enzymes that are known to be different in women with endometriosis than women without endometriosis represent examples of such factors. For example, some women with endometriosis have carbonic anhydrases characterized by defective ligands. ("Salivary Carbonic Anhydrase Isoenzyme," *The Journal of Physiology,* 520, Part 2, pp. 315-320, 1999, Kivela et al.) Carbonic anhydrase II and IV have been documented to be different in peritoneal fluid and in serum obtained from women with endometriosis. Carbonic anhydrase enzymes also play a role in managing buffer capacity in saliva. (Archives of Oral Biology, 48(8): 547-51 (2003)) Women with endometriosis, who have immune deficiencies in certain carbonic anhydrase types, reportedly possess saliva with different kinds of ligands on the carbonic anhydrase when compared to carbonic anhydrases in the saliva of women without endometriosis. (J Physiol., 299:29-44, February 1980) Further, lower secretion levels of saliva by women with endometriosis can also affect how buffer capacity is controlled in saliva. Based on experimental evidence for effects of carbonic anhydrase inhibitors on phosphate buffer levels in sheep, it can be speculated that decreases of carbonic anhydrase levels in saliva of women with endometriosis might also lead to a proportionally greater percent of phosphate based buffer in the saliva. (*The Effect of Carbonic Anhydrase Inhibitors on the Anionic Composition of Sheep's Parotid Saliva. With an Appendix on Uncatalysed Carbon Dioxide-Water Kinetics* by P. T. McTigue. J R Blair-West, R T Fernley, J F Nelson, E M Wintour, and R D Wright) In accordance with certain embodiments of the invention, these differences, both in the composition and types of carbonic anhydrase present in saliva, are the subject of an initial screening procedure for identifying some immune deficiencies that correlate to endometriosis. These deficiencies/differences in the carbonic anhydrases are observed by comparing response patterns for electrophoresic SDS gel studies in saliva samples from women with and without endometriosis. It can be noted that the band for carbonic anhydrase (s) is weaker in women with endometriosis.

Another factor that affects (or is affected by) the pathology of endometriosis is the metabolism of estradiol, which is regulated both by the menstrual cycle, and by tissues that produce estradiol and stimulate the growth of endometrial lesions. Approximately 90 percent of the estradiol in saliva is in a free unbound state, making saliva a good medium for measuring changes in estradiol activity. ("Evolution of Salivary Estradiol Levels During the Spontaneous Menstrual Cycle. Correlation Between Saliva and Plasma," *J. Gynecol Obstet. Biol. Reprod (Paris*), 18(1):47-52, 1989, J. Berthonneau, F. Begon, J. Y. Bounaud, J P. Chansigaud, L. Cedard) Saliva is also a good medium to compare different estradiol metabolites such as catechol estradiol, estrone or estriol, which appear to be different between women with and without endometriosis. A discussion of the differences observed in estrone to estriol ratios in women with endometriosis is found in "Estrogen Production and Metabolism in Endometriosis," *Endometriosis Annals of the New York Academy of Sciences,* 955:75-85 (2002), 2002 New York Academy of Sciences, S. Bulun, S. Yang, Z. Fang, B. Gurates, M. Tamura, and S. Sebastian, Departments of Obstetrics and Gynecology and Molecular Genetics, University of Illinois at Chicago, Chicago, Ill. 60612, USA Without necessarily wishing to be bound by any theory, it is believed that estradiol forms metabolites 2-hydroxy and 4-hydroxy catechols, which have been implicated in endometriosis pathogenesis and the growth of ectopic endometrial lesions. The presence of these metabolites can stimulate cell proliferation. The interaction of certain metabolites of estradiol with the cells of the misplaced ectopic lesions compounds the disease and leads to added stress and side effects that cause inflammatory responses that circulate in the blood and serum to other parts of the body, including saliva, thus causing additional injury to the immune system. ("The Pains of Endometriosis," *Science,* 308 (5728): 1587-1589, 2005, K. Berkley, A. Rapkin, R. Papka)

The 2-hydroxy and 4-hydroxy catechols are believed to transform into 2-methoxyestradiol, which is found in increased levels in the luteal phase of the menstrual cycle. Presumably, this transformation occurs in order to protect the body from any toxic effects of estradiol itself. A discussion of how these different forms of estradiol metabolites interact with each other is set forth in "Cardiovascular Pharmacology of Estradiol Metabolites," *Journal of Pharmacology and Experimental Therapeutics,* 308:403-409, 2004, R. Dubey, S. Tofovic, E. Jackson.

A distinction between women having endometriosis and women not having endometriosis relates to their ability to convert catechol forms of estradiol into 2-methoxyestradiol. Women with active endometriosis have defects in their ability to control free estradiol metabolite formation. For example, women with active endometriosis are deficient in 17-beta hydroxysteroid dehydrogenase-2 (17 beta-HSD-2), thus limiting the metabolic pathway to convert estradiol to methyoxyestradiol. As a consequence, women with active endometriosis have excess 4-catechol estradiol, especially in the luteal phase compared to women without active endometriosis.

Without necessarily wishing to be bound by any theory, it is believed that the excess catechol levels in women having endometriosis leads to the chelation of metallic ions that are otherwise responsible for the proper function of certain prosthetic enzymes, such as carbonic anhydrase. Hence, it is believed that it is the excess catechol estradiol levels may be at least partially responsible for the carbonic anhydrase deficiencies and defects discussed above.

The existence of excess catechol levels can be detected using flavonoid pigments that change in response to different catechol estradiol concentrations. The degree to which color responses occur, whether discerned via the eye or quantitatively measured, can be used as a screening means or marker in evaluating for the presence or absence of endometriosis. For example, according to an embodiment of the invention discussed in greater detail below, spectral absorbency values measured for flavonoids such as malvidin-3,5-diglucoside mixed with saliva can be correlated with different phases in the menstrual cycle that reflect differences in how saliva responds to increased estradiol concentrations. Without wishing to be bound by theory, it is believed that endometrial inflammation causes the production of glycosidases in saliva, and glycosidases react with malvidin-3,5-diglucoside to form malvidin-3-glucoside in women with endometriosis to generate clear or faded colored products. The chelation of metallic ions (caused by catechol estradiol forms discussed above) could destabilize certain prosthetic enzymes in saliva, causing the color of the anthocyanins (a species of flavonoids) to fade.

To investigate this relationship between flavonoid pigments and changes in estradiol metabolism, experiments were carried out to determine the relationship between flavonoid pigment color stability and free estradiol levels in saliva. The data is illustrated in and explained in reference to FIG. 5. The left set of data is a plot based on saliva mixed with 0 pg/ml of estradiol, the middle set of data points is a plot based on saliva mixed with 2 pg/ml of estradiol, and the right set of data points is a plot based on saliva mixed with 4 pg/ml of estradiol. Samples were taken over a 30 day period for each set of data. The ordinate represents percent change in flavonoid pigment stability between color absorbance measurements taken at $t_1=0$ and $t_2=30$ minutes.

Figure 5:
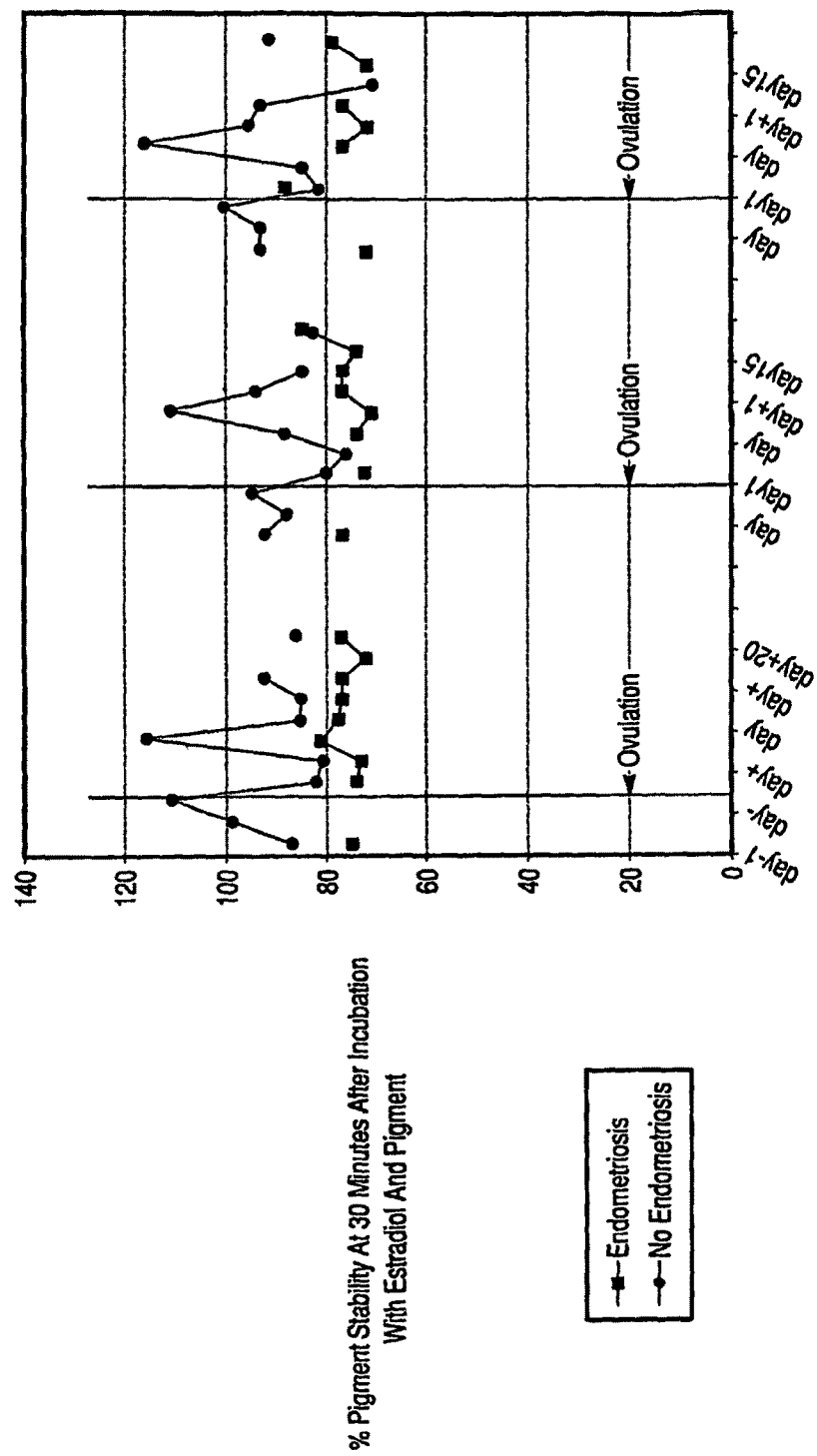
FIG. 5 shows plots comparing pigment stability versus cycle day in saliva samples mixed with different concentrations of estradiol, the saliva samples taken from women with and without endometriosis.

As shown in FIG. 5, pigment mixed with saliva from women with endometriosis did not show significant variation in its stability between the follicular and luteal phase of the menstrual cycle, regardless of the concentration of estradiol added. That is, the amount of estradiol added to the saliva-pigment mixture did not significantly affect differences in the stability of the pigment in the follicular and luteal phases. Stability tended to range between 70 and 80 percent. On the other hand, women without endometriosis had a greater variation between the follicular and luteal phase of the cycle in flavonoid pigment stability because the body fluid contains enzymes that respond differently to estradiol in different phases of the menstrual cycle. It is believed that women with endometriosis have deficiencies in these enzymes.

Further, pigment stability, i.e., as measured as the difference in absorbance between time 0 and time 30 minutes, is consistently lower for women with endometriosis. As shown in FIG. 5, it has been observed that the pigment can exceed 100% stability due to gains in intensity over time, e.g., between the 0 and 30 minute measurements. For example, the pigment stability of a woman not having endometriosis at two days before ovulation with no additional incubation of estradiol was 110% (i.e., the absorbency value at t=0 was 0.522, and at t=30 was 0.578.) This pattern of increase in color absorption was observed in the saliva from women who do not have endometriosis before ovulation if no additional estradiol was incubated in the saliva. This pattern of increased color absorption was also found when the saliva was incubated in different concentrations of estradiol three days after ovulation.

Additionally, some women with endometriosis have other factors that affect fertility and prevent an embryo from implantation in the uterus. These factors are also due to an immune problem that differs from the above-described immune problems resulting in misplaced ectopic tumors, but still are associated with the presence of endometriosis.

Endometriosis screening procedures that may be performed on saliva and other bodily fluids and matter, collectively referred to as bodily samples, are described in detail below. Each screening procedure is in theory designed for the evaluation of one or more physiological factors, and more particularly factor imbalances, present in the bodily samples of women with endometriosis. As described above, the factor imbalances are believed to be responsible for or caused by certain forms of estradiol and imbalances in estradiol metabolite levels, inflammation, immune deficiencies that correlate with the presence of endometriosis, and other symptoms of endometriosis.

Turning now to the drawings, FIG. 1 generally depicts a platform that can hold an array of multiple samples for permitting multiple tests (assays) to be carried out on the platform with respect to a bodily sample or multiple bodily samples of a subject. The assays may provide quantitative, semi-quantitative, and/or qualitative analysis. The use of multiple assays permits testing for multiple factors responsive to, responsible for, or otherwise correlating to or indicative of endometriosis. As a result, the test results taken in their totality provide an accurate and a more complete assessment as to whether or not the tested patient is afflicted with endometriosis significantly enough to warrant therapy or monitoring for further investigation. For example, where a first assay serves to detect for a first physiological factor not possessed by an individual, the individual may still be reliably diagnosed with endometriosis by the second assay which detects for a different second physiological factor. Furthermore, the use of different types of assays which measure different factor imbalances allows for a broader perspective as to the etiology of the disease in a particular individual. By multi-testing for more than one factor, it is possible to discern whether or not the responses are specific to endometriosis or some other condition that may have similar symptoms to endometriosis, but which is not endometriosis. Repeated testing over an extended time period permits determination of whether or not the response is getting progressively stronger or weaker, thereby indicating whether or not a certain therapy or treatment is effective. Consequently, the patient may be advised as to whether or not she has endometriosis or whether or not a treatment therapy is effective.

FIG. 1 shows a platform 10 preferably made of a transparent material, such as glass or plastic (e.g., acrylic, vinyl, acetate, or carbonate compound) inert with respect to aqueous solutions having a pH between 4 and 9. It is also preferred that platform 10 undergoes no degradation over a wide temperature range, such as from about −20° C. to about 80° C., for instance at least about 20° C. to about 60° C.

Platform 10 as illustrated is a preferred implementation for carrying out multiple testing procedures, each directed to the detection or measurement of a respective physiological factor. It should be understood that it is within the scope of the invention to modify platform 10 to permit for one, two, three, or more samples to be collected and retained for each of the testing procedures/assays. It is also within the scope of the invention to modify platform 10 to hold multiple bodily samples for a single testing procedure, or a single bodily sample for a single testing procedure. Further, other arrangements than shown may be selected. For example, the assays may be arranged concentrically with respect to one another.

Platform 10 includes a first set of wells 12, which is described below as used in conjunction with pH testing, although it should be understood that wells 12 may serve other purposes and testing procedures. Wells 12, and for that matter the other wells 14, 16, 18 included on platform 10, are not particularly limited to a specific size or shape. Wells preferably are capable of holding disposable and removable cuvettes, tubes, or ampules with volumes ranging from 1 microliter (µl) to 1000 microliters (µl) of solution, e.g., from 25 to 100 microliters (µl) of solution suitable for many testing procedures. Wells 12, 14, 16, 18 may be formed in removable slides, e.g., glass slides, to permit relocation of the slide to a microscope for observation. The opening area of wells 12, 14, 16, 18 at the upper surface of platform 10 is preferably about 3 mm to about 10 mm in diameter, to provide an opening area of about 2.25 $mm^2$ to about 25 $mm^2$, e.g., about 1 $cm^2$. It should be understood that wells 12, 14; 16, 18 may possess different diameters from one another and vary in capacity. Further, wells 12, 14, 16, and/or 18 may have non-circular openings, e.g., oval, square, etc. Platform 10 may possess a greater or lesser number of wells 12, 14, 16, 18 for each screening procedure.

Figure 2:
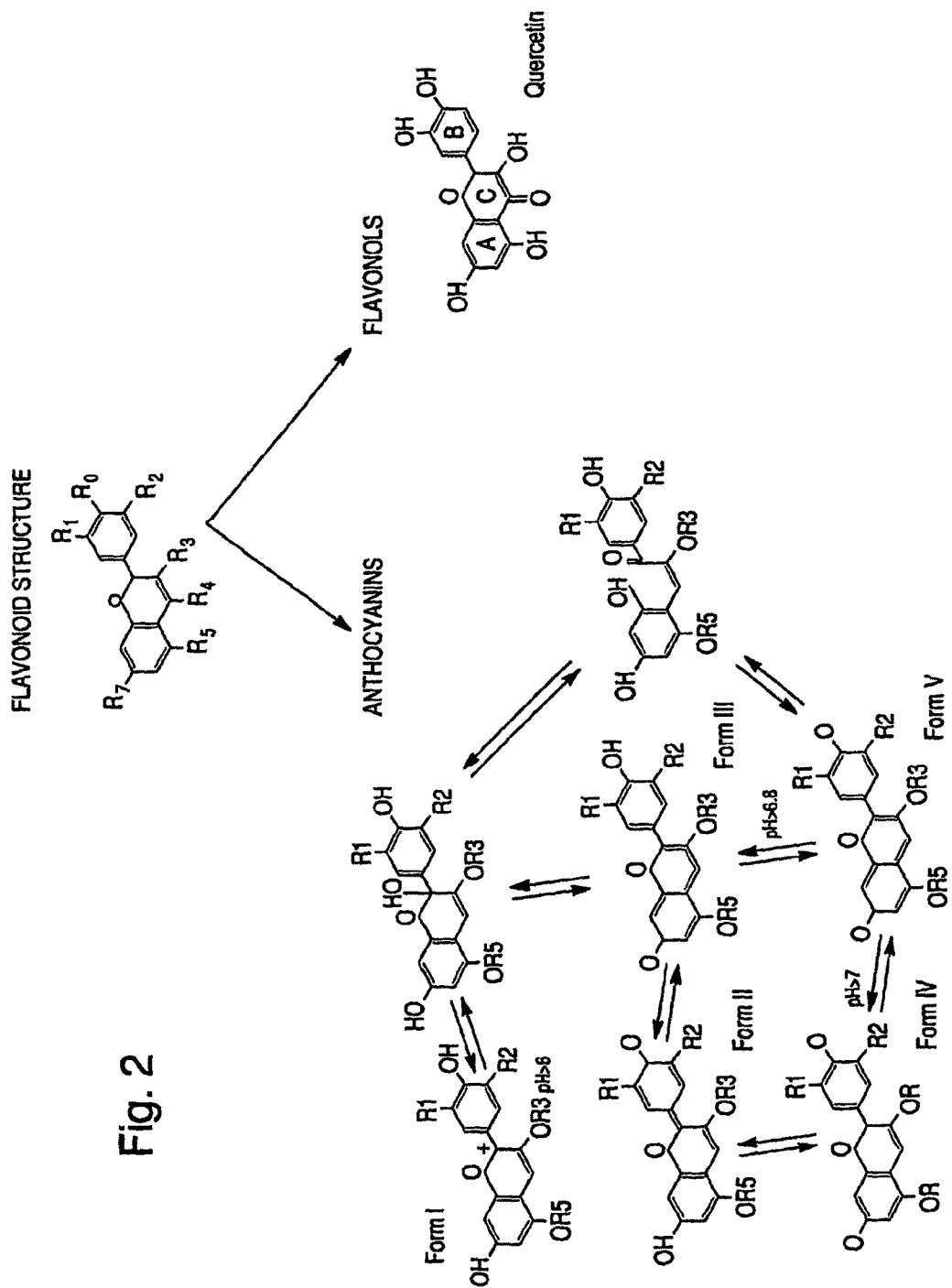
FIG. 2 shows chemical structures of flavonoids and transformations experienced by anthocyanins over different pH ranges.

Testing procedures will be described in greater detail below. Several of the procedures involve the use of pigments, including flavonoids such as anthocyanins. Chemical structures for flavonoids, including the flavonol quercetin, are shown in FIG. 2. The transformations experienced by anthocyanins are also shown in FIG. 2. The Markush groups of the flavonoids, including the anthocyanin structures, may be defined as follows: $R_0$ is selected from the group consisting of hydrogen, hydroxy, and keto group; $R_1$ is selected from the group consisting of hydrogen, hydroxyl, and $C_1$-$C_4$ alkoxy; $R_2$ is selected from the group consisting of hydrogen, hydroxyl, and $C_1$-$C_1$ alkoxy; $R_3$ is selected from the group consisting of hydrogen, hydroxyl, or glycoside selected from the group consisting of glucosides, rutinosides, arabinosides, sophorosides, p-coumaroyl rutinosides, and rhamnosides; $R_4$ is a keto group in flavonoids including quercetin; $R_5$ is selected from the group consisting of hydrogen, hydroxyl, and a glycoside selected from the group consisting of glucosides; and $R_7$ is selected from the group consisting of hydrogen, hydroxyl, a keto group and $C_1$-$C_4$ alkoxy.

The color exhibited by the different pigment forms is pH sensitive. Form I favors a pink color and is dominant below pH 4.0. Form II favors a purple color and is dominant between pH 5.5-7.0. Form III favors a blue to purple color and is dominant between pH 6.8-7.2. Forms IV and V are deep blue and favored above pH 7.2. Forms II and III are known as anhydrous base forms, whereas Forms IV and V are referred to as ionized anhydrobase forms, which can be stabilized through chemical interaction with substances such as chelating agents, such as divalent metallic ions, co-pigmenting with reducing sugars or phenolic compounds, or by association with certain charged molecules that have glycosides. The degree to which stabilization occurs is dependent upon ionic strength, pH, and concentration of the pigment and stabilizing agent. As described above, women with endometriosis have catechol estradiol imbalances which can lead to chelation of the catechol estradiols with some metallic ions, thus causing the anhydrobase Forms IV and V to be less stabilized.

The concentration of pigment for embodiments described herein involving the use of anthocyanins preferably yet optionally falls within the range of $8 \times 10^{-6}$ molar to $1 \times 10^{-3}$ molar. When the pigment is provided in an aqueous solution, such as saliva, the pigment is preferably yet optionally present at levels between $8 \times 10^{-5}$ molar and $1.0 \times 10^{-4}$ molar at pH levels between 5.0 and 9, more preferably between 5.8 and 8.0. The pigment may be combined with methanol to provide a $1 \times 10^{-3}$ molar concentration, then optionally diluted with water or saliva to the concentration levels mentioned above, for example. If methanol preparation is diluted in the saliva to form an aqueous solution, the methanol acts as a surfactant. It should be understood that agents other than methanol may be selected for making the solution, and that dilution in an aqueous solution is also optional. Further, it is within the scope of the invention to employ the anthocyanins without the addition of methanol or other agents.

The structure of the flavonoid quercetin is set forth below and reproduced in FIG. 2:

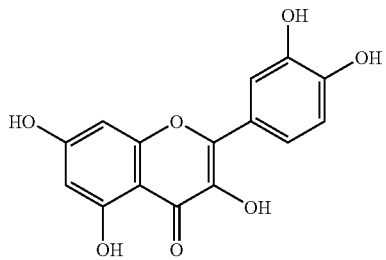 [SMILES: O=c1c(O)c(-c2ccc(O)c(O)c2)oc2cc(O)cc(O)c12]

1. Denaturing Effect—pH Testing

A first embodiment of the invention provides an endometriosis screening method comprising subjecting a bodily sample to a denaturing procedure, and measuring a property such as pH of the bodily sample after, and optionally before, the denaturing procedure. Without wishing to be bound by any theory, it is believed that the denaturing procedure relies on the sensitivity, such as temperature sensitivity, of certain physiological factors that experience imbalances in women with endometriosis.

According to an implementation of this embodiment, the denaturing procedure is designed to cause certain heat sensitive enzymes that appear to be relevant for maintaining buffer capacity in saliva to denature, while having no substantial effect on the phosphate buffer levels in the same saliva sample. As mentioned above, certain carbonic anhydrase enzymes control buffer capacity in saliva and are found to be different in saliva from woman with endometriosis compared to the saliva of a woman without endometriosis. The denaturing procedure has been observed to have a greater effect on the saliva pH levels of a healthy woman than on the saliva pH levels of a woman with endometriosis. Without wishing to be bound by any theory, it is believed the denaturing may be caused by differences in ionic strength that result because of the differences in buffer controlling mechanisms in saliva with and without endometriosis, dependent upon interactions with certain heat sensitive enzymes. Whereas the denaturing procedure neutralizes the buffering effects of certain enzymes or buffer controlling proteins in healthy women, thus altering the saliva sample pH when it is exposed to air, the buffer control mechanism in samples from women with endometriosis is left substantially unaffected by the denaturing procedure. Consequently, the denaturing procedure will produce less change in the pH of the saliva that is exposed to air in women with endometriosis.

A freezing and thawing cycle is an example of a denaturing procedure that will cause certain buffer maintaining enzymes such as carbonic anhydrases to denature, as well as some other calcium sensitive components to precipitate out of the saliva solution. Using wells 12, endometriosis is screened by assessing how well or poorly a bodily fluid sample maintains buffer capacity when subjected to one or more freezing and thawing cycles. Saliva samples are collected over a period of consecutive days and each sample is aliquotted into a separate one of wells 12. In FIG. 1, four wells 12 are shown for receiving samples taken over four consecutive days. It should be understood that platform 10 may contain a lesser or greater number of wells 12. Further, samples may be taken at different intervals, e.g., the daily sampling may be replaced by sampling every 48 hours. Preferably, a first pH sample is taken prior to the first freezing and thawing cycle. Each of the samples is subjected to a first freezing and thawing cycle, and a second pH value is recorded. The sample is optionally subjected to one or more additional freezing and thawing cycles, and a third and optionally subsequent pH value(s) is/are recorded. The difference between pH values is calculated and recorded. As shown in Table 1 below, the first and second pH values used were taken subsequent to a first thaw and subsequent to a fourth thaw, respectively. In the experiments summarized in Table 2 below, the first and second pH values were taken subsequent to a first thaw and a second thaw, respectively. These results are compared with a patient without endometriosis (a man). It should be understood that the values may be taken prior and subsequent to subsequent thaws. Additionally, more than one freezing and thawing cycle may be conducted between measurement of the pH values

EXAMPLE 1

A preliminary study of thawed saliva samples from ten women with histories of endometriosis found an increased frequency of low changes in pH of thawed saliva samples. This is documented in the following Table 1 that tracks pH changes in thawed saliva from a woman with a history of endometriosis. pH measurements were taken with a pH meter. The procedure for collecting and processing the saliva samples is set forth below.

1. First morning whole saliva is collected passively by putting an absorbent pad under the tongue. The saliva is allowed to collect into the pad.
2. The absorbent pad is put into a container having a plunger which compresses the pad to expel the saliva.
3. The extracted saliva is centrifuged at 7500× for 30 minutes.
4. After centrifugation the pH is measured and recorded.
5. The processed saliva sample is then frozen at −20° C.
6. After the sample has been frozen for at least 24 hours, the sample is thawed to room temperature in an ice bucket for about an hour.
7. When the sample has thawed a second measurement of pH is made and recorded.
8. An evaluation is made of the difference between the two pH measurements.

It has been observed that samples obtained from women having endometriosis have a high percent of difference values that are less than 0.2, in some instances approximately 0 or negative, as noted in the Table 1 below.

TABLE 1 pH changes in saliva from women with endometriosis

| Cycle day | pH 1st thaw | pH 4th thaw | Change in pH |
|---|---|---|---|
| −10 | 7.35 | 7.59 | 0.24 |
| −9 | 7.35 | 7.60 | 0.25 |
| −8 | 7.24 | 7.56 | 0.32 |
| −7 | 7.30 | 7.31 | 0.01 |
| −6 | 7.19 | 7.10 | −0.09 |
| −5 | 7.21 | 7.19 | −0.02 |
| −4 | 7.05 | 7.04 | −0.01 |
| −3 | 7.02 | 7.08 | 0.06 |
| −2 | 7.44 | 7.25 | −0.19 |
| −1 | 7.21 | 7.22 | 0.01 |
| LH spike | 6.82 | 7.15 | 0.33 |
| +1 | 6.86 | 6.82 | −0.04 |
| +2 | 6.59 | 6.71 | 0.12 |
| +3 | 6.82 | 6.95 | 0.13 |

The above test procedures were repeated on saliva samples taken from a woman known to not have endometriosis and from a man. After repeated thawing cycles, considerably higher pH values were observed. The results are reported in Table 2 below.

TABLE 2 pH changes in saliva samples from people with no endometriosis

| Sample day | 1st thaw | 2nd thaw | Difference in pH |
|---|---|---|---|
| Woman without endometriosis ||||
| 1 | 7.22 | 7.68 | 0.44 |
| 2 | 7.25 | 7.36 | 0.11 |
| 3 | 6.90 | 7.65 | 0.75 |
| 4 | 7.25 | 7.84 | 0.59 |
| 5 | 7.29 | 7.84 | 0.55 |
| 6 | 7.46 | 8.01 | 0.55 |
| Man ||||
| 1 | 6.96 | 7.22 | 0.26 |

TABLE 2-continued pH changes in saliva samples from people with no endometriosis

| Sample day | 1st thaw | 2nd thaw | Difference in pH |
|---|---|---|---|
| 2 | 7.06 | 7.23 | 0.17 |
| 3 | 6.73 | 7.08 | 0.35 |
| 4 | 7.10 | 7.43 | 0.33 |
| 5 | 6.62 | 7.01 | 0.39 |
| 6 | 6.82 | 7.22 | 0.40 |

As exhibited by Table 1 above, women who have endometriosis show a high frequency of pH changes of 0.2 or less between repeated freezing and thawing of saliva samples, whereas as shown in Table 2 saliva samples from subjects without endometriosis exhibited pH changes upon freezing and thawing that tended to register at 0.3 and higher, even when subjected to only a single freezing and thawing cycle.

These tests are preferably conducted on samples collected daily over a period of at least one week, preferably at least two weeks to minimize deviations that could be caused by outside influences, such as time of day. It should be understood that while a pH meter was used for measuring pH values in the above example, other quantitative approaches or semi-quantitative or qualitative measurement approaches may also be implemented. For example, conductivity meters may be selected. Other commercial pH indicators that use color changes can also be used, although the indicator preferably is capable of measuring pH changes within a 0.2 deviation between pH values ranging from 5.8 to 8.

2. Denaturing Effect: Crystallography

According to another embodiment of the invention, crystallography of a saliva sample is examined as part of an endometriosis screening procedure. Depending upon the cycle phase and whether the subject has endometriosis, crystal formations can be observed in saliva samples subjected to a denaturing procedure, such as a freezing and thawing cycle, or dehydration under ambient conditions. Crystals form when metallic ions such as sodium, calcium or other bivalent metallic ions are in solution with available soluble sugars. This condition can result when glycosidase enzymes break glycosidic bonds in glycoproteins thus allowing for the presence of soluble sugars in the saliva. Inflammation can cause an increase in glycosidases in saliva. "*Enzymatic protective systems of saliva in inflammation of the periodontium*", Patol Fiziol Eksp Ter., 1991 January-February; (1):32-4, Vavilova T P, Petrovich IuA, Malyshkina L T.

Without wishing to be bound by any theory, it is believed that women with endometriosis appear to have factors in saliva that allow these crystal formations to occur at any time during the menstrual cycle, possibly because there are higher levels of glycosidases, due to inflammatory factors resulting from endometriosis. *Glycosidases in the peritoneal fluid from infertile women with and without endometriosis*, Clin Biochem., 1998, 31(3):181-6 (ISSN: 0009-9120) Brandelli A; Passos E P. In contrast, women who do not have endometriosis only show the characteristic ferning patterns of crystals just before ovulation when increased estradiol levels lead to increased activity of glycosidases, and about a week later on the day of implantation, presumably because of a surge in estradiol production about 7 days after ovulation. Temporal Surge of Glycotransferase Activities in the Genital Tract of the Hamster during the Estrous Cycle, Biology of Reproduction 54, 1032-1037 1996, Daulat, Tulsiani, Catherine Chayko, Marie-Claire Orgebin-Crist Yoshihiko Araki.

According to an implementation of this embodiment of the invention, wells 20 are provided for conducting the crystallinity assay to detect for the presence or absence of endometriosis. A 25 microliter sample of saliva having been subjected to a freezing and thawing cycle is deposited in one or more of wells 20 and allowed to dry and crystallize at ambient (e.g., room) temperature. These wells are designed to be viewed under a microscope at 200× magnification. Using a microscope, it is possible to visually see distinctive crystal shapes and patterns that are produced, depending upon whether or not the female subject has endometriosis and the cycle phase from which the sample was obtained.

It has been observed that women having endometriosis exhibit crystal formations in their dried saliva in the luteal phase, and often in or throughout the other phases of the menstrual cycle. Generally, women with endometriosis have saliva characterized by crystals that extend outward radially from a center or hub of the crystal in multiple directions so that the distal ends of the crystals form a generally rounded or polygonal outline around the center. These crystal formations are also referred to herein as axial formations due to the branching out of crystals from a central axis.

Figure 14A:
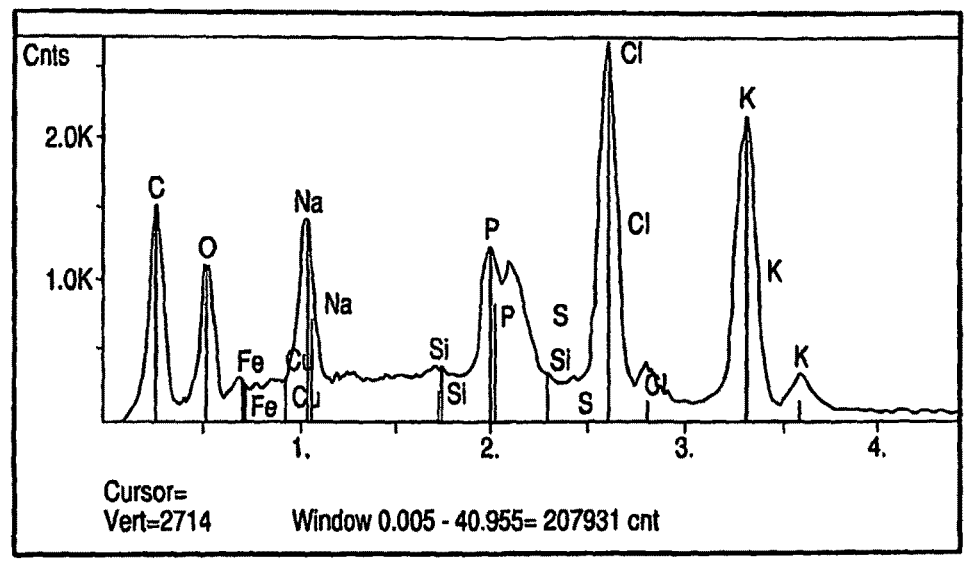
FIGS. 14A and 14B are comparative spectra measurements for a saliva sample taken from a woman not having endometriosis and a woman with endometriosis, respectively.
Figure 14B:
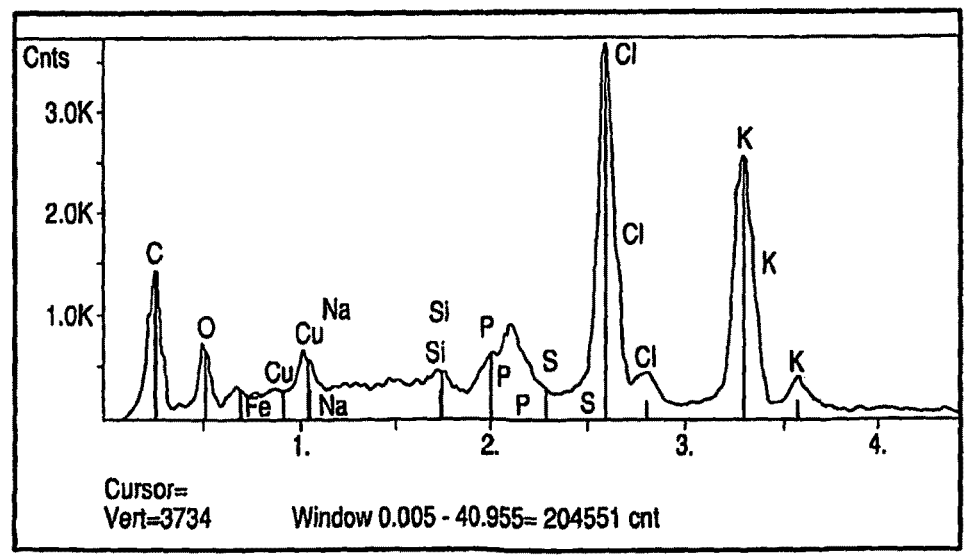

On the other hand, women not having endometriosis exhibit crystal formations in their dried saliva only immediately before the fertile stage, and for one day which occurs at the time of implantation, about one week after ovulation. Generally, the crystal formations for women not having endometriosis often are less dense and more linear than crystal formations of women having endometriosis. These linear crystal formations possess an elongate spine with branch pendent crystals extending outward generally perpendicular to the spine to provide a generally fern-like or skeletal appearance. Referring to FIGS. 14A and 14B, the elongated or fern-like crystal formations of women not having endometriosis are documented to contain proportionally higher levels of sodium salts than women having endometriosis. FIGS. 14A and 14B are comparative spectra measurements for a saliva sample taken from a woman not having endometriosis and a woman having endometriosis, respectively. Spectral analysis was conducted using electron microscope and a light element detector system (SEM/EDS). The woman without endometriosis had a relatively high sodium (Na) peak, as seen in FIG. 14A, compared to the relatively low sodium (Na) peak of FIG. 14B for the woman having endometriosis.

Figure 9:
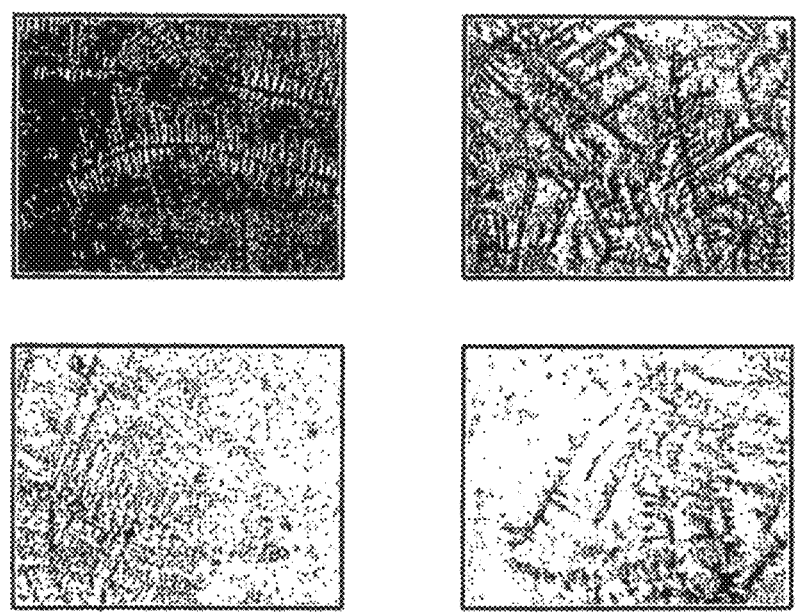
FIG. 9 are reference photographs taken at 200× magnification of saliva crystals observed in samples from women without endometriosis in the fertile phase.

Women having endometriosis also tend to have a high frequency of the crystal formation that can be axially oriented as compared with a low frequency of any type of crystal formation observed in women who do not have endometriosis. This visual distinction is best viewed under a microscope at 200× magnification. FIGS. 6, 8, and 10 provide reference photographs of saliva crystals observed in samples from women with endometriosis in the follicular, fertile, and luteal phases, respectively. Crystal formations were observed in each of the phases, with the crystals generally showing the axial formation. FIGS. 7, 9, and 11 provide reference photographs of saliva crystals observed in samples from women without endometriosis in the follicular, fertile, and luteal phases, respectively. In the follicular and luteal phases shown in FIGS. 7 and 11, respectively, little or no crystal formation was observed. FIG. 9 depicts the fertile phase in which less dense crystals characterized by a spine and branches was observed.

Procedures for collecting the saliva samples for this embodiment were as follows.

1. One milliliter samples of whole saliva are collected in the morning and stored in a plastic ampoule. The time and date are noted on each sample. It is possible to let the sample sit for a few hours, or prepare the saliva sample immediately for crystal observation by drying a small amount on a glass slide. It is also possible (yet optional) to freeze the sample and then thaw it as described below.

2. The freezing temperature and thawing rate are variables affecting the outcome of the crystallization process. See *Art of Science*, Vo. 11, No. 2, HyClone Laboratories Inc., "Freezing and Thawing Serum and Other Biological Materials", p. 1-4 (Spring 1992). To account for these variables, freshly collected saliva was centrifuged at 7500×G for 30 minutes. The centrifugation allows different size particles to settle in more uniform order, thus permitting for more standardized procedures in the pipetting process. The supernatant was frozen to −20° C. Thawing was conducted within 1 hour at room temperature and ambient conditions.

3. A 0.25 microliter sample of thawed saliva is pipetted from the top part of the saliva sample onto well 20 of a slide, and allowed to dry under ambient conditions for at least one hour.

4. The dried saliva is viewed in a microscope at 200× power.

5. Optionally a digital camera attached to a computer can be attached to the microscope and a digital photograph on the computer records the view on the slide.

6. The digital photos of the samples are viewed on a computer using a commercial software program.

7. The samples are compared to a digital reference library that has reference photos stored to serve as comparisons for determining what type of crystal formation is prevalent in the sample. If the crystal formation shows axial formation, it is highly probable that the sample originated from a woman suffering from endometriosis. If the crystal formation is linear with parallel line formations, then the sample originated from a woman not suffering from severe endometriosis. If there is no crystal formation observed, it is also highly probable that the sample originated from a woman not suffering from endometriosis.

8. A record is kept of the type of crystal observed, what cycle day it originated from, and the frequency that the crystal formation is observed within a given phase of the menstrual cycle. The dried saliva samples may keep the crystalline patterns intact for years and can be stored for future reference.

9. If a predetermined number (e.g., three or more) of dried samples have crystal formations that match (or do not match) the reference photographs, an assessment can be made as to whether or not the saliva originates from a woman with endometriosis.

It should be understood that the freezing and cooling cycle described in the above procedure is only one example of a denaturing procedure imparted on the sample.

EXAMPLE 2

The photo analysis process was performed on 10 women, each of whom provided 30 samples from different days of the menstrual cycle. Five (5) of the women had endometriosis, and 5 of the women did not have endometriosis. The photos were catalogued as to cycle day which had been calculated according to results for ovulation detection performed using urine-based commercial ovulation tests. A measurement was made for the frequency (% slides with crystal formation) for any given cycle day in the study.

TABLE 3

| CYCLE DAY based on urinary LH levels | % saliva samples from women with endometriosis who had some form of crystal formation observed in the sample | % saliva samples from women without endometriosis who had some form of crystal formation observed in the sample |
|---|---|---|
| −5 | 20% | 10% |
| −4 | 10% | 0% |
| −3 | 0% | 10% |
| −2 | 60% | 10% |
| −1 | 60% | 20% |
| 0 1 day before ovulation | 80% | 80% |
| 1 | 50% | 0% |
| 2 | 60% | 20% |
| 3 | 60% | 0% |
| 4 | 80% | 0% |
| 5 | 100% | 0% |
| 6 | 60% | 0% |
| 7 | 60% | 0% |
| 8 | 80% | 0% |
| 9 | 80% | 20% |
| 10 | 60% | 0% |

Figure 12:
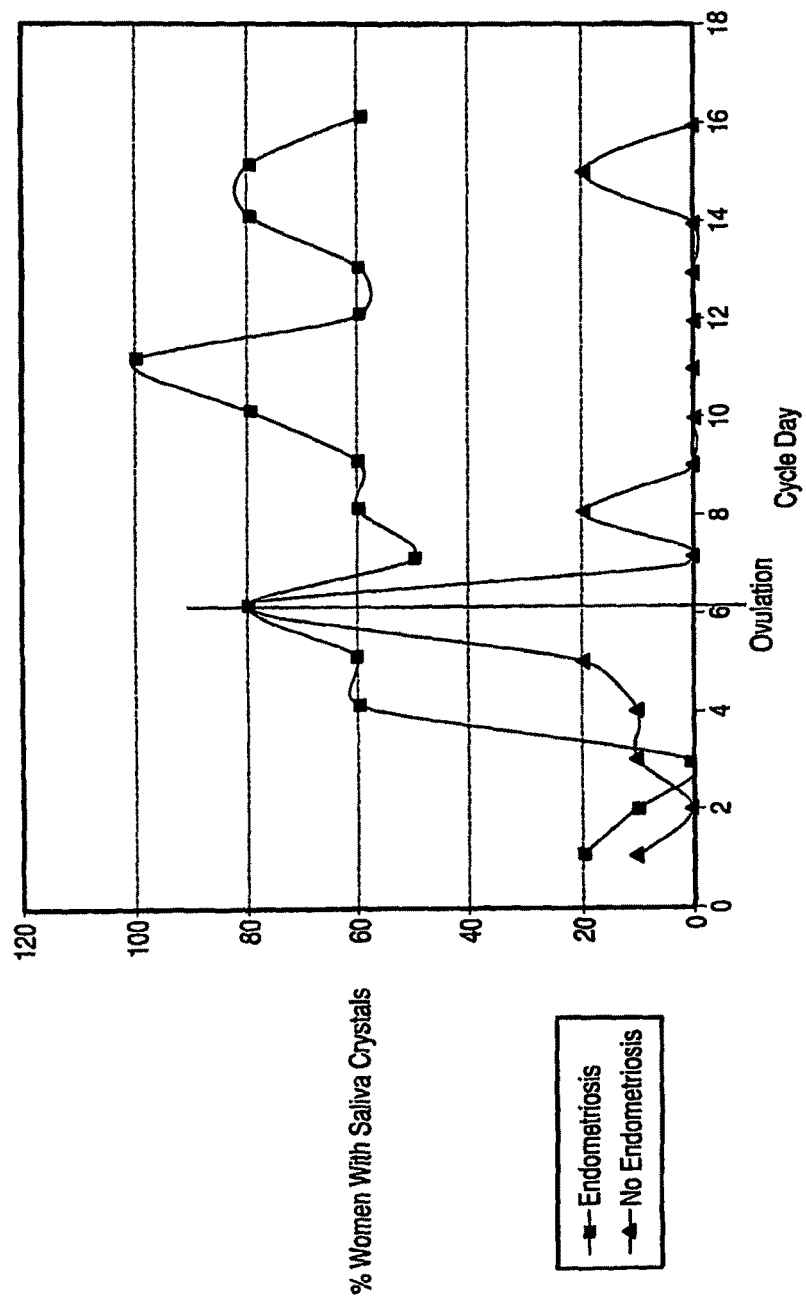
FIG. 12 is a graph illustrating the relationship between saliva crystal formation and menstrual cycle for women with and without endometriosis.
Figure 13A:
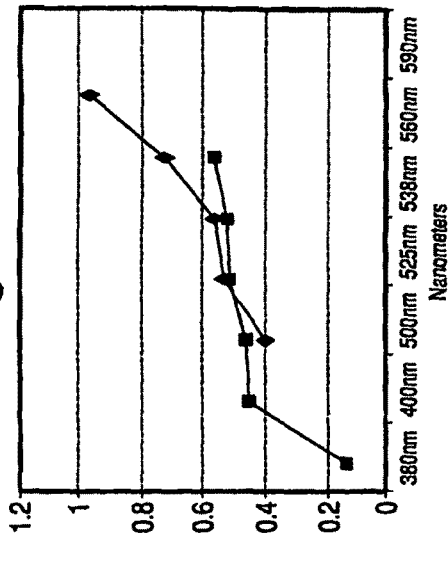
FIG. 13a-13d are graphs comparing absorbency between 400 nm and 600 nm for several women with and without endometriosis.
Figure 13B:
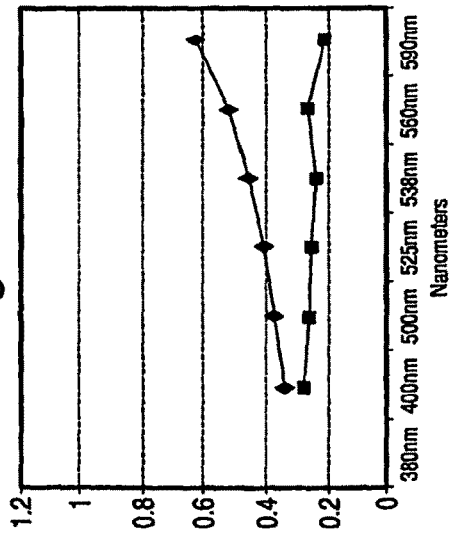
Figure 13C:
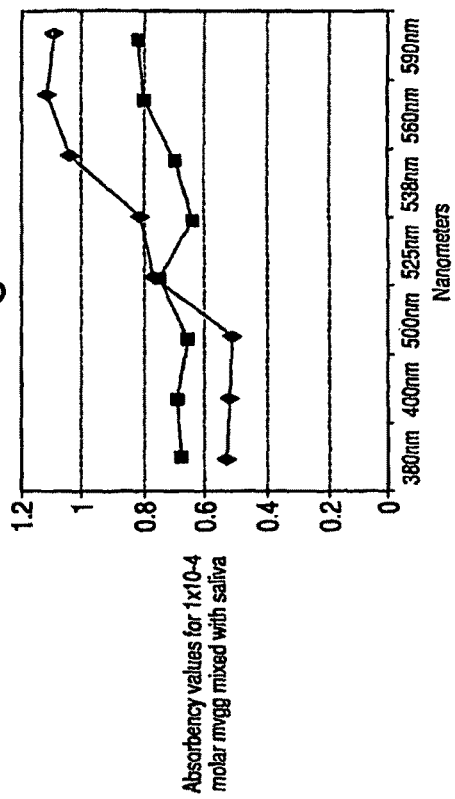
Figure 13D:
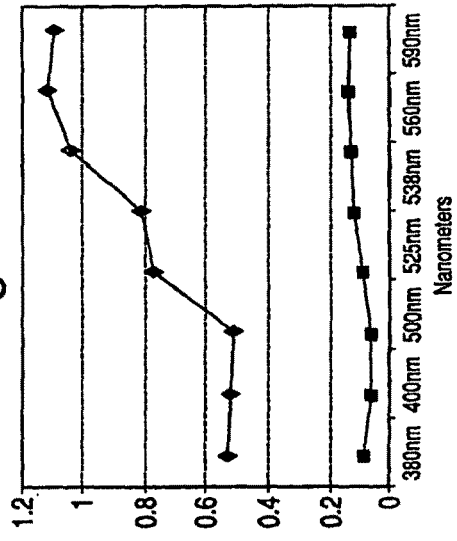

The slides were transferred to a microscope, and the frequency of any visible crystal forms on glass slides prepared according to procedures described above was counted. The data of Table 3 is set forth in graphical form in FIG. 12 to illustrate the frequency of any crystal form observed in each of the two groups of women: women with and without endometriosis. As seen in FIG. 12, women with endometriosis exhibited crystal formations throughout each phase of the menstrual cycle, whereas women with no endometriosis exhibited greatly reduced and less dense crystal formations for significant portions of the menstrual cycle, in particular the leuteal phase.

3. Optical Density Comparison

Another embodiment of an endometriosis screening method of the present invention features a comparison of two optical density peak values between 400 nm and 700 nm of a bodily fluid mixed with a flavonoid pigment as part of an endometriosis screening procedure.

Referring to FIG. 1, any of wells 12, 14, 16, and/or 18 may be selected for carrying out this embodiment. Samples of saliva or another bodily fluid are obtained from a woman, preferably periodically over at least a five-day span, and the samples are pipetted into the wells or disposable cuvettes or tubes that fit into wells 12, 14, 16 and 18. The samples are mixed with a flavonoid pigment, which is preferably evenly pre-impregnated into the well, cuvette, or tube.

Impregnation of the pigment into the well or disposable cuvette or tube is carried out as follows:

1. A defined amount of pigment that is weighed to reach a $1 \times 10^{-3}$ molar concentration for 1 ml sample is mixed with 1 ml of methanol.
2. The pigment mixture is vortexed until all the pigment is dissolved.
3. A defined volume of this solution is pipetted into the well or disposable tube or cuvette.
4. The solution is allowed to evaporate so that the pigment is evenly distributed on to the surface of the well or disposable cuvette or tube.
5. The well, tube or cuvette having the evaporated pigment distributed onto it can now be stored for several months under cool dry conditions until ready for use.

When samples are ready for evaluation, the samples are pipetted in defined amounts into the wells, disposable tubes or cuvettes so that the resulting concentration of the dried pigment is reconstituted to be at $1 \times 10^{-4}$ molar concentration.

The samples are then measured with a spectrophotometer for absorbency values read between 400 nm and 700 nm. A comparison is made between two different wavelengths on the same sample in order to determine the rate of change in the absorbency value between different wavelengths. The chart below compares ratio values of 600 nm/400 nm for saliva samples mixed with the anthocyanin malvidin 3,5-diglucoside and quercetin.

TABLE 4

| Cycle Day | Endometriosis - Malvidin 3,5-diglucoside | No Endometriosis - Malvidin 3,5-diglucoside | Endometriosis - Quercetin |
|---|---|---|---|
| −10 | 1 | | |
| −9 | 1.25 | | |
| −8 | | 5.14 | |
| −7 | | | |
| −6 | | | 0.91 |
| −5 | 1.21 | 5.19 | |
| −4 | 2.18 | | |
| −4 | 2.53 | 1.5 | |
| −3 | 2.1 | 2.8 | 0.22 |
| −2 | | | |
| −1 | | 2.05 | 0.33 |
| 0 | | 1.2 | |
| +1 | | 3.3 | |
| +2 | | | |
| +3 | | 5.85 | |
| +4 | | | |
| +5 | 3.72 | 5.15 | |
| +6 | | | |
| +7 | | | |
| +8 | 1.21 | | |
| +9 | 1.33 | | |
| +10 | 1.22 | 5.15 | |
| +11 | | | |
| +12 | | 5.21 | |
| +13 | 3.33 | | |

FIG. 13 provides further examples of absorbency patterns between 400 nm and 600 nm for women with endometriosis and women without endometriosis. The specimens from women without endometriosis increased at a greater rate, or had a greater slope, between 400 nm and 600 nm than the specimens from women with endometriosis over the same range.

Without wishing to be bound by any theory, it is believed that the ratio values represent the degree to which certain anhydrobase forms of anthocyanins are present in the sample. Referring back to FIG. 2, the ratio values represent the stability of certain anhydrobase forms of anthocyanins, and in particular Forms II and III in relationship to the ionized anhydrobase Forms IV and V, when data is taken within the range of 400 to 700 nm. The ratios, when considered in conjunction with the cycle day the bodily fluid was taken, permit an assessment to be made as to whether or not a woman has endometriosis.

Figure 3:
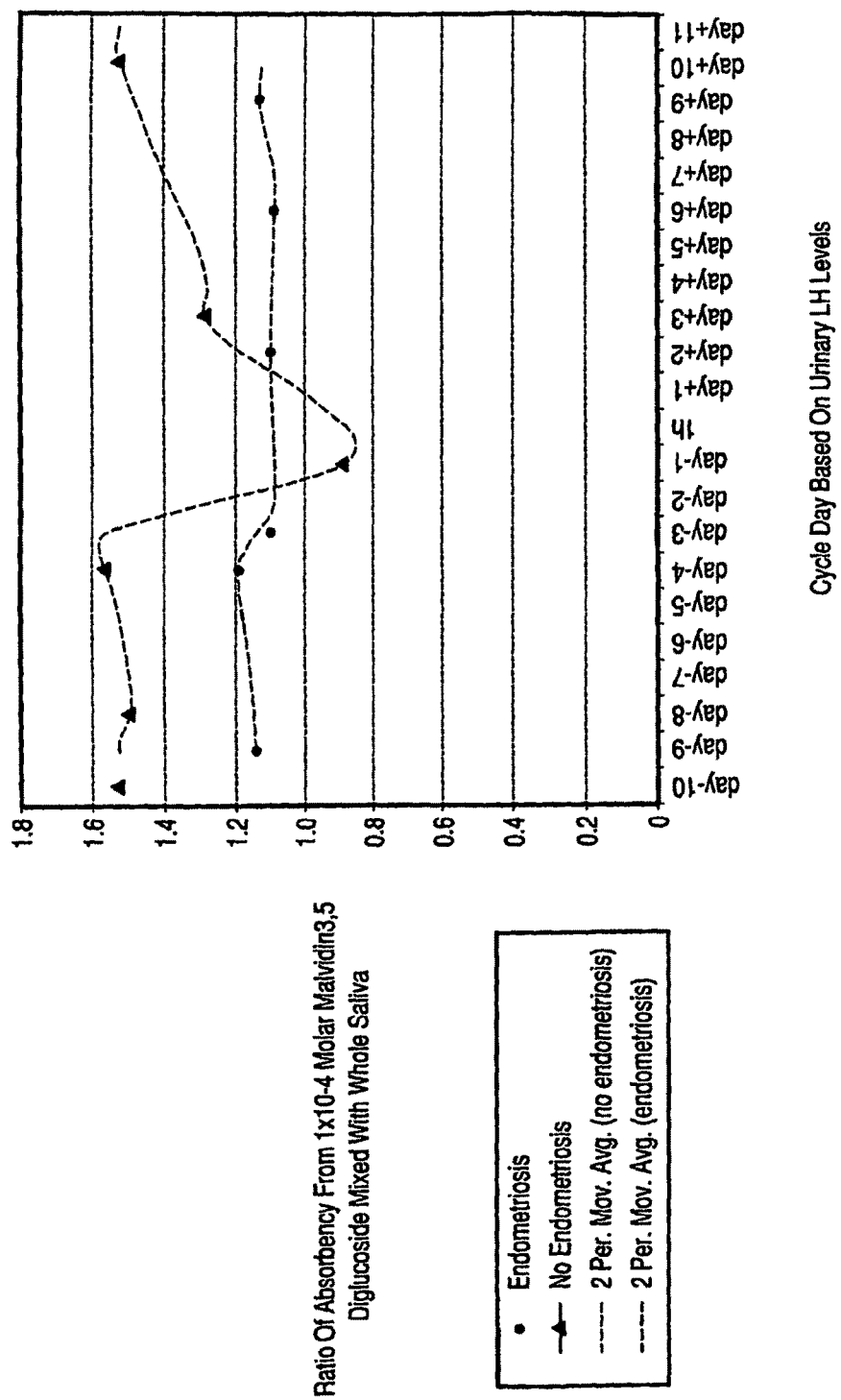
FIGS. 3 and 4 are graphs plotting ratios of absorption (560 nm/538 nm) of an anthocyanin pigment mixed with saliva samples from women with and without endometriosis over parts of their menstrual cycles.

For example, it has been observed that women with endometriosis provide uniform 560 nm/538 nm ratio values for saliva samples mixed with $1 \times 10^{-3}$ molar concentration of the anthocyanin, malvidin 3,5-diglucoside. Specifically, the 560 nm/538 nm ratio values are generally about 1 throughout the cycle, more broadly between about 1 and about 1.2 for the women with endometriosis. On the other hand, saliva samples from women who do not have endometriosis can be mixed with the same anthocyanin pigment in identical concentrations to produce 560 nm/538 nm ratio values ranging from 0.8 to 1.7, with the values mostly ranging between 1.2 and 1.5, depending on the cycle day, ionic strength, and the pH of the saliva sample. Referring to the examples shown in FIGS. 3 and 4, the ratio ranges from 1.2 to 1.5 in the non-fertile phase of the menstrual cycle (after ovulation has occurred). The ratio shifts below 1, i.e., 0.8 to 1.0 in the ovulatory phase of the cycle shown in FIG. 3.

Figure 4:
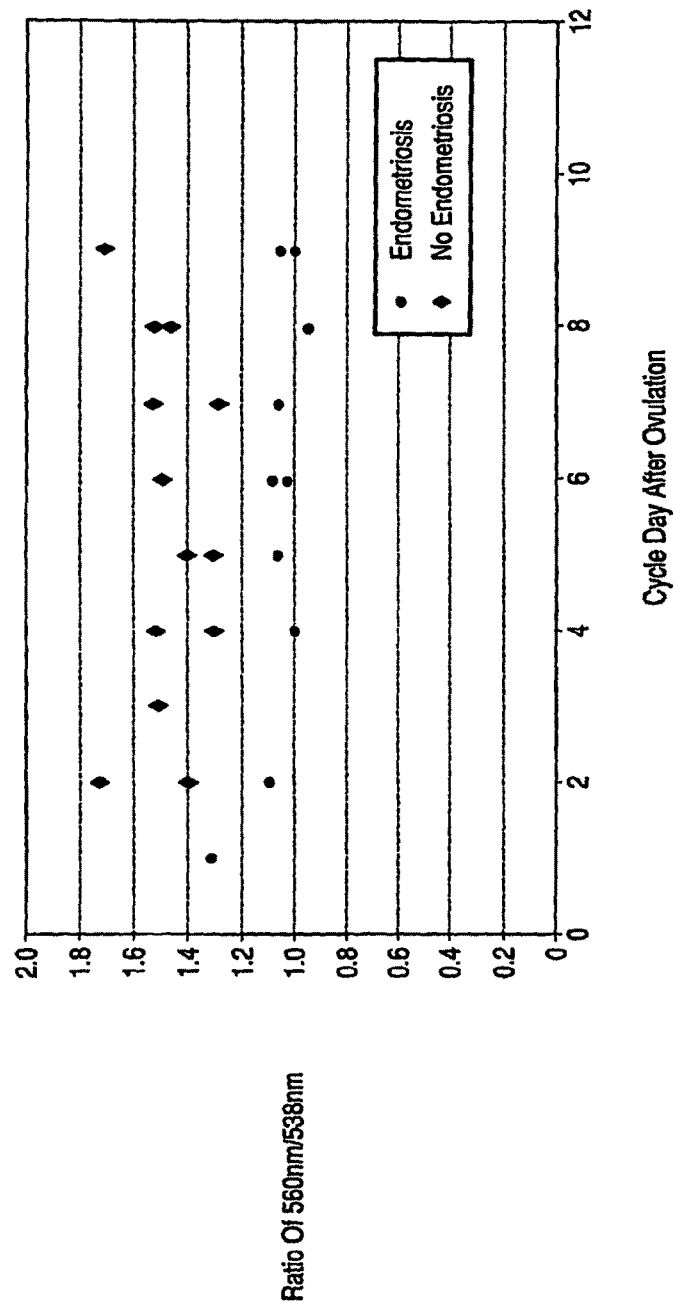

Without wishing to be bound by theory, a more detailed explanation of the chemistry follows. Anhydrobase anthocyanin Forms II and III are in equilibrium with one another in a pH range of 4<pH<7. The anhydrobase Form III has a maximum absorption at about 556 nm and the anhydrobase Form II has a maximum absorption at about 534 nm. As illustrated in FIG. 4, when anthocyanin pigment is combined with saliva of a woman suffering from endometriosis, equilibrium is favored towards equal distribution between anhydrobase Form II and anhydrobase Form III, which produces a ratio close to 1, more generally between 1 and 1.2. This is pH independent within the range from pH 5.8 to 7.8. It is believed that the higher absorbency ratio values, e.g., greater than 1.3, of women without endometriosis is the result of greater stabilization of anhydrobase III relative to anhydrobase II.

Without wishing to be bound by theory, it is believed that the difference in the ratio values observed between women with endometriosis and women who do not have endometriosis may be due to some differences in ionic strength, which may affected by certain immune factors present in saliva that are sensitive to changes in ionic strength and pH regulation. Differences in the composition of enzymes between saliva samples from women with and without endometriosis may cause structural changes in the flavonoid pigments that can be used as chemical markers to distinguish between women with endometriosis from women without endometriosis.

The following experiments evaluated the effect of heat on the above-described biological mechanism which controls the ratio of the anhydrobase forms.

The saliva samples are mixed with anthocyanin pigment malvidin 3,5-diglucoside. Each sample is placed in 1 ml tube. Optical density measurements are taken at a wavelength between 500 nm and 600 nm. Measurements are made at 538 nm and 560 nm. The measurements are taken both before and after the samples are subjected to a cycle of heating at over 100° C. for 20 minutes and cooling to ambient temperature. Measurements are reported below in Table 5.

TABLE 5

|  | 538 nm | 560 nm | ratio value |
|---|---|---|---|
| woman with endometriosis |  |  |  |
| not heated | 0.18 | 0.185 | 1.0 |
| heated buffer | 0.175 | 0.16 | 0.9 |
| not heated | 0.13 | 0.19 | 1.46 |
| heated | 0.16 | 0.23 | 1.44 |
| woman with no endometriosis |  |  |  |
| not heated | 0.14 | 0.17 | 1.21 |
| heated | 0.10 | 0.10 | 1.00 |

The results of the unheated and heated saliva samples of Table 5 show that heating has a minimal effect on the absorption patterns for the buffer, with a difference of 0.02 in the ratio value. In contrast, the saliva of the woman not having endometriosis showed a 10 fold decrease in absorbency ratio of 0.21 as the result of the heating. The saliva sample from the woman with endometriosis showed a decrease in ratio value of 0.01, similar to the decrease observed in the heated buffer. There appear to be heat sensitive factors present in the unheated sample of saliva from the woman without endometriosis that affect stabilization of the anhydrobase form III.

While data comparison is described above as involving a calculation of the ratio of absorption readings at the wavelengths of 560 nm and 538 nm, it should be understood that the absorption data may be subject to other forms of data manipulation and mathematical functions (e.g., subtraction) for comparison. Additionally, the above procedures and calculations of ratio values can also be performed at other wavelengths between 400 and 700 nm, and with other types of anthocyanins, or flavonoids, realizing that different types of flavonoids would have different ratio values because of the differences in the λ max value. The mechanism and basis for determining these values would, however, remain the same. Reference values for different wavelengths and different wavelength ratios can be obtained by measuring or otherwise obtaining data from women known to have endometriosis and known not to have endometriosis.

EXAMPLE 3

Procedure for measurements was as follows:

1. The saliva sample is thawed in an ice bucket.

2. A record is made of the pH of the sample.

3. Depending on the volume of the well, between 90 microliters to 450 microliters of saliva can be pipetted into a well or disposable cuvette or tube that fits into a well. The well or disposable tube or cuvette has a defined amount of malvidin 3,5-diglucoside at 10% concentration to yield a $1 \times 10^{-4}$ molar concentration. 2.76 mg of crystal form malvidin 3,5-diglucoside may be dissolved in 1 ml of methanol and mixed with 3 ml ethylene glycol monoethyl ether (EGME). The solution is then aliquotted into each well, cuvette or tube at the appropriate volume ratio, while allowing the solvent to evaporate. Once the malvidin 3,5-diglucoside is contacted to the cuvette or tube and kept in cool dry conditions at room temperature, it can remain intact and ready for use for long periods of time.

4. The sample mixed with the pigment is measured in a spectrophotometer or plate reader at the wavelengths 560 nm and 538 nm.

5. A calculation is made as to the ratio for absorbance for 560 nm/538 nm. If the ratio value >1.25 for samples taken in the luteal phase, the sample is preliminarily determined to be from a woman who does not have active endometriosis, preferably subject to additional sample testing with consistent results. If the ratio value is less than 1.2, the sample may be preliminarily determined to be from a woman who has active endometriosis. If a predetermined percentage, e.g., 3/5 (60% or more), of the samples taken during consecutive days of the luteal phase provide ratio values for absorbency as measured at 560 nm/538 nm of less than 1.2, then the samples reflect the presence of endometriosis. On the other hand, if 0/5 consecutive days of the luteal phase give ratios between 1.0 and 1.2, then a conclusion is drawn that the samples originate from a woman who does not have endometriosis.

Table 6 below represents the ratio 560 nm/538 nm for women having (right column) and not having (left column) endometriosis. Saliva samples were mixed with $1 \times 10^{-4}$ molar concentration of malvidin-3,5-diglucoside. Each row in Table 6 corresponds to a cycle day:

TABLE 6

| No Endometriosis | | | Endometriosis | | |
| --- | --- | --- | --- | --- | --- |
| Cycle Day | Trial #1 | Trial #2 | Cycle Day | | |
| Day −14 | | | Day −14 | | |
| Day −13 | | | Day −13 | | |
| Day −12 | | | Day −12 | | |
| Day −11 | | | Day −11 | | |
| Day −10 | | | Day −10 | 1.22 | 1.1 |
| Day −9 | | | Day −9 | 1.13 | |
| Day −8 | 1.3 | 1.5 | Day −8 | | |
| Day −7 | | 1.5 | Day −7 | 1.2 | |
| Day −6 | | | Day −6 | | |
| Day −5 | | | Day −5 | 1.06 | |
| Day −4 | 1.35 | 1.53 | Day −4 | 1.09 | 1.02 |
| Day −3 | 1.3 | | Day −3 | 1.13 | |
| Day −2 | 1.2 | | Day −2 | | |
| Day −1 | 1.1 | | Day −1 | | |
| Day 0 | 0.8 | 1.06 | Day 0 | | |
| Day +1 | 1.4 | 1.2 | Day +1 | | |
| Day +2 | 1.15 | 1.28 | Day +2 | 1.1 | |
| Day +3 | 1.4 | 1.25 | Day +3 | | |
| Day +4 | 1.3 | | Day +4 | | |
| Day +5 | 1.4 | 1.72 | Day +5 | 1.09 | |
| Day +6 | 1.5 | | Day +6 | | |
| Day +7 | 1.3 | 1.5 | Day +7 | 1.0 | |
| Day +8 | 1.4 | 1.32 | Day +8 | 1.08 | |
| Day +9 | 1.5 | | Day +9 | 1.03 | 1.08 |
| Day +10 | 1.3 | 1.52 | Day +10 | 1.07 | |
| Day +11 | 1.5 | 1.47 | Day +11 | 0.95 | |
| Day +12 | 1.7 | | Day +12 | 1.05 | 1 |

Testing was performed on 10 women known not to have endometriosis, and 5 women known to have endometriosis. Of the former group reported in Table 6, 27 out of 30 samples (i.e., 90%) taken produced results with ratio values for 560 nm/538 nm of 1.2 or greater. This data is consistent with other data measuring the same ratio values for woman not having endometriosis. It should be noted that ratio values for women who do not have endometriosis will have values near 1 about one day before ovulation, during ovulation and immediately after ovulation. Without wishing to be bound by any theory, it is believed this is because the composition of saliva changes during the ovulation period due to the effects of 17 beta estradiol on certain enzymes such as glycosidases and some prosthetic enzymes. As a result, stabilization of the anhydrobase is compromised and the ratio value is diminished during ovulation. Therefore, it is best to measure differences between women with and without endometriosis after ovulation in the luteal phase, because during the luteal phase, saliva from women who do not have endometriosis is able to stabilize the anhydrobase form; whereas saliva from women who have endometriosis still has factors present that inhibit anhydrobase stabilization. Of the 20 out of 30 samples measured in the luteal phase, 19 of the 20 samples produced a ratio of 560nm/538 nm of greater than 1.2. Of the latter group of women having endometriosis, 10 out of 10 samples reported in Table 6 taken during the luteal phase (i.e., 100%) were characterized by a ratio of less than 1.2, as expected.

FIG. 4 is a graph plotting the ratio of absorption at 560 nm to 538 nm for woman with endometriosis and a woman without endometriosis through the luteal phase of the menstrual cycle. The selected pigment was malvidin 3,5-diglucoside, which was mixed with the saliva samples to give a $1 \times 10^{-4}$ molar concentration. The woman who did not have endometriosis exhibited ratios of absorption (560 nm/538 nm) repeatedly ranging between about 1.3 and about 1.6. A relative stable blue color was observed. In contrast, the woman with endometriosis repeatedly exhibited ratios of absorption (560 nm/538mm) in a range of 1 and not exceeding 1.2, and although a blue color response temporarily resulted, the response was not stable and the blue faded over a matter of 20 minutes. Without wishing to be bound by any theory, it is believed that the fading of color was caused by the lack of stabilizing metal ions.

4. Indicator-Activated Color Changes

The following embodiment of the invention provides an endometriosis screening procedure based on the ability of certain pigment-indicator combinations, such as quercetin with diluted iodine, to alter the color of the pigment mixed with the bodily fluid sample, preferably saliva.

Quercetin can be used as a marker for certain types of peroxidases, which are inflammatory substances found at elevated levels in women having endometrial inflammation. One example is interleukin L-6 production which is known to be inhibited by certain flavonoids such as luteolin and quercetin. ("Luteolin Inhibits an Endotoxin-Stimulated Phosphorylation Cascade and Proinflammatory Cytokine Production in Macrophages", *Pharmacology: Therapeutics*, Vol. 296, Issue 1, 181-187, January 2001, A. Xagorari, A. Papapetropoulos, A. Mauromatis, M. Economou, T. Fotsis and C. Roussos) Strips 22 provide colorimetric system assays for endometriosis detection that use flavonoids to detect inflammatory responses resulting from endometriosis. Each strip 22 comprises a matrix such as ashless cellulose, cellulose acetate, or nylon mesh embedded with a pigment, such as quercetin or an anthocyanin. The saliva sample and the flavonoid pigment are combined on strip 22. It is preferred to embed the pigment into strip 22 before the saliva is added. The pigment may be embedded onto the cellulose as follows.

Quercetin is dissolved in a methanol solution to provide, for example, a $1 \times 10^{-3}$ molar concentration. Twenty microliters are pipetted onto the cellulose absorbent surface, and the methanol is allowed to evaporate until dry. Once strip 22 is prepared, a body fluid sample is applied. By way of example, the sample size may be 25 microliters. After about 5 seconds, an approximately equal amount of diluted tincture of iodine (e.g., 1:10 concentration) is added.

Cellulose or nitrous cellulose treated with quercetin yields a yellow color that is stable under ambient conditions. The addition of the saliva sample does not significantly alter the yellow color, regardless of whether or not the woman supplying the sample has endometriosis. However, the color response produced by addition of the diluted iodine tincture differs between a woman having endometriosis and a woman not having endometriosis. In the case of a sample collected from a woman not having endometriosis, the diluted iodine tincture will cause strip 22 to turn immediately a stable blue. On the other hand, for a woman having endometriosis, strip 22 will not yield a blue color. Instead, within approximately 5 seconds the color response will begin to fade to yellow and continue to maintain this yellow color over a period of time such as 30 minutes. Time and intensity may vary from sample to sample. However, any degree of fading at all can be associated with some form of inflammation response relating to endometriosis.

Preferably, multiple color response tests are conducted and evaluated before making a conclusion. For example, a series (e.g., five or more) of color responses yielding yellow or faded yellow color responses from multiple saliva samples collected from a woman over consecutive days may be interpreted as evidence that the female subject may have endometriosis. A series (e.g., five or more) of samples, collected over consecutive days, yielding a deep blue color in response to the addition of diluted tincture of iodine may be interpreted as evidence that the subject does not have endometriosis.

Without wishing to be bound by any theory, it is believed that the instability of the sample from the woman with endometriosis is due to elevated peroxidase levels that relate to increased cytokines present in saliva as a result of inflammatory responses to the presence of endometriosis.

5. Chromatography

Additionally, it is possible to measure for presence of endometriosis by using chromatography techniques to evaluate how a flavonoid interacts with the saliva sample. The chromatography can also be performed on a solid matrix system such as ash-free-cellulose in strip 22. As described above, 25 microliters of $1\times10^{-3}$ molar solution of quercetin is pipetted at a defined location on strip 22. A marker (e.g., pencil mark) may be applied to record the location of the quercetin mark. Then 25 microliters of fresh whole saliva is pipetted just below the quercetin mark. A solution of butanol, acetic acid and water in ratios 4:1:5 respectively is allowed to filter through the paper. The distance that the front travels versus the distance that the quercetin travels is measured. The Rf value is defined as the ratio of the front distance divided by the distance that the pigment travels.

The Rf value corresponds to a measurement that can predict whether or not a woman is suffering for inflammation related to endometriosis. Women with endometriosis having inflammation show Rf values closer to the standard buffer value ranging between 0.5 and 1.0. Women who do not have endometriosis and do not have inflammation from endometriosis show values much lower than the standard control of around 0.2, usually in a range of 0.2 to 0.4.

TABLE 7

| Standard Rf for quercetin Control sample: buffer at same pH as bodily fluid | Rf for quercetin mixed with saliva from woman with no endometriosis | Rf value for quercetin mixed with saliva from woman with endometriosis before hysterectomy | Rf value for quercetin mixed with saliva from woman with endometriosis after hysterectomy |
|---|---|---|---|
| 0.92 | 0.22 | 0.72 | 0.18 |
| 0.92 | 0.26 | 0.72 | 0.10 |
| 0.8 | 0.28 | 0.75 | 0.38 |
| 1 | 0.25 | 0.40 | 0.50 |
| 1 | 0.27 | 1.0 | 0.37 |
| 1 | 0.24 | 0.50 | 0.40 |
| 1 | 0.25 | 0.8 | 0.25 |
| 1 | 0.23 | 1.0 | Na |

As can be noted in the data in Table 7, the woman who has endometriosis shows significantly higher Rf values for quercetin on the chromatography assay than the woman who did not have endometriosis. After a hysterectomy, the Rf values declined for this woman. It can be noted that the Rf values after the hysterectomy were in some cases lower than the Rf values obtained from the woman with no endometriosis.

The variability in the Rf values for the woman with endometriosis may correlate with certain factors that vary from day to day such as inflammation responses to the way the immune system responds to certain environmental factors that affect women predisposed to endometriosis. It has been noted that women who have hysterectomies to control for endometriosis can still generate other physiological responses and imbalances in their immune system that are not controlled by just the removal of reproductive organs. The data in Table 7 suggests that hysterectomy had an effect that diminished the Rf values for quercetin, but that the woman is still predisposed, although to a lesser degree, to whatever responses quercetin may generate in saliva from a women with endometriosis.

6. Filtration

Strips 24 placed on platform 10 provide for additional colorimetric system assays that involve an absorbent surface with a filtering mechanism. According to a preferred embodiment, the absorbent surface can comprise a Sephadex® (cross-linked dextran gel) preparation having antigens that respond to factors found in the saliva of women without endometriosis, but not found in saliva of women having endometriosis (or vice versa). A saliva sample is contacted with and allowed to pass through strip 24. The saliva sample is brought into contact with a color response system both before and after passing through the Sephadex® filter strip 24.

A comparison is made between the color response systems to determine whether any color changes occurred as the result of the sample passing through strip 24, and an interpretation is made as to whether or not the saliva originated from a woman with endometriosis.

The absorbent surface of strips 24 can also be designed to remove certain factors that might interfere with the assay. For example it might be necessary or desired to remove certain molecules such as those greater than 100,000 Daltons in order to assay for only those components in the saliva that have sizes smaller than 100,000 Daltons. By imposing a molecular sieve into strip 24, one can adapt the assay to meet these requirements.

By way of example, certain divalent metallic components that are sensitive to the absence or presence of endometriosis can be removed by filtering. This is especially true for certain calcium-dependent factors. By putting EDTA (a calcium chelation agent) inside the strip one can remove or denature any calcium dependent factors that affect the assay. An indicator that produces different color responses depending upon whether the calcium-dependent factors is present is selected and used to treat the sample before and after filtration. The color responses both before contact with the EDTA and after contact with the EDTA are compared.

Platform 10 may possess a greater or lesser number of strips 22, 24 than shown in FIG. 1.

Collection of Samples

The procedure for collecting saliva from an individual is not particularly limited. The saliva sample may be placed in a container extracted in measured or random amounts. For example, a person may spit into a tube and then use a pipette to extract a defined amount of saliva such as 100 microliters, and optionally deliver the sample to the desired well. It is also be possible to use a device that absorbs saliva directly inside the mouth, such as a suction device or a device that uses osmotic pressure to transport saliva into a pouch that has a fixed volume. Another technique is to absorb saliva onto a sponge or vessel that has multiple capillary tubes that hold fixed amounts of saliva. Saliva can also be absorbed using an absorbent material, which is then inserted into a tube with a plunger to push the saliva out of the absorbent.

The timing of the saliva collection can be particularly important, both in terms of its relationship to the menstrual cycle (as discussed above) and in terms of the time of day, e.g., morning or evening. ("Circadian Rhythms in Human Salivary Flow Rate and Composition," *The Journal of Physiology* 220, 529-545, 1974, Dawes, C.; "The effects of flow rate and duration of stimulation on the concentrations of protein and the main electrolytes in human submandibular saliva," *Archives of Oral Biology*, 19, 887-895) Saliva changes in its composition according to time of day. It has been observed and documented that collection of unstimulated saliva taken from under the tongue provides the most consistent results. Additionally, it is preferred to collect the samples in the morning before eating any food. Alternatively, at least a period of 20 minutes from food intake should elapse before samples are taken. It is additionally preferred not to stimulate the saliva through any means. A passive collection system works well for the assays defined in this invention.

It should be understood that the saliva multi-based assay system has multiple presentations. It can be used in different formats than illustrated in the attached drawings. For example, platform 10 can also have a circular shape or be a tube whereby the indicators are located inside the tube. It is also possible to omit one or more of the illustrated assays, and/or include additional assays for screening of endometriosis. Further, each of the assays can be isolated on its own platform without other assays.

A series of samples compared in multiple assays on one platform offers several benefits. By assessing different factors simultaneously from a saliva sample and comparing these factors to additional samples taken periodically, e.g., daily, it is possible to generate more accurate and more definitive assessments as to whether or not a woman has endometriosis. Such a system with multiple assays not only generates more information about the condition of an individual, but also reduces the time and cost in the process of evaluating for the presence of endometriosis. Furthermore, the use of different types of assays allows for a broader perspective as to the etiology of the disease in a particular individual. For example, distinctions can be made as to whether or not the individual is suffering from immune deficiencies and inflammatory responses, or whether the endometriosis is related to defects in estradiol metabolism or not. Additionally, results of these tests can assist a practitioner in determining whether or not a certain therapy is effective in treating a particular individual who may be suffering from endometriosis.

The non-invasive based assay system with multiple assays according to preferred embodiments of the invention offers great improvements over current technologies that evaluate women with endometriosis. The system can provide a test that allows for home-based collection of samples taken over a period of days or weeks of a menstrual cycle. While some tests may be evaluated in home use, others may be delivered to the doctor or laboratory for testing. Importantly, the woman is not required to visit the doctor on a daily basis to provide bodily fluid sample; rather, these samples may be taken at home, so that the test subject need not visit the doctor or laboratory until after all samples have been collected. The system may be designed solely of assays that allow for home-based evaluation so as to allow a woman to make a preliminary evaluation as to whether or not she might be subject to endometriosis in that particular cycle and should therefore see a specialist who can advise her on possible treatments. It is also possible to perform these measurements in a doctor's office where the woman can have immediate evaluation as to whether on not the pain she is having or her infertility problem is due to endometriosis or due to some other cause. The system and methods of various embodiments of the present invention are also useful for use during routine physical examinations, and thereby promote early stage intervention.

The procedures and systems described herein are based on the premise that many factors are present in the pathogenesis of endometriosis. Some of these factors are sensitive to estrogen metabolism imbalances which can be tracked by measuring ratio of ionized anhydrobase forms of certain anthocyanins. Other factors involve differences in immune factors such as ligands and glycosides present on certain temperature-sensitive enzymes that in turn are sensitive to the presence of certain metallic ions. When catechol estrogens interfere with the functioning of these enzymes, other cellular processes are affected and a cascade of immune responses and inflammatory responses occur, resulting in other markers to indicate endometriosis.

The procedures and systems herein distinguish between these different factors to screen for the presence of endometriosis at high accuracy.

The flavonoids and anthocyanin pigments used in several embodiments of the invention may be obtained from various commercial sources, such as, for example, Sigma Aldrich and Polyphenols in Norway. Other sources may also be used.

The foregoing detailed description of the preferred embodiments of the invention has been provided for the purposes of illustration and description, and is not intended to be exhaustive or to limit the invention to the precise embodiments disclosed. The embodiments were chosen and described in order to best explain the principles of the invention and its practical application, thereby enabling others skilled in the art to understand the invention for various embodiments and with various modifications as are suited to the particular use contemplated. It is intended that the scope of the invention cover various modifications and equivalents included within the spirit and scope of the appended claims.

What is claimed is:

1. A method of screening for endometriosis in a female subject, comprising:
   subjecting a bodily sample to a denaturing procedure;
   measuring a property of the bodily sample prior and subsequent to the denaturing procedure;
   comparing the property measured prior and subsequent to the denaturing procedure; and
   evaluating said comparison of the property for endometriosis in the female subject.

2. The method of claim 1, wherein said subjecting of the bodily sample to the denaturing procedure comprises subjecting the bodily sample to at least one freezing and thawing cycle, and wherein said measuring comprising obtaining a first pH measurement of the bodily sample prior to the freezing and thawing cycle and obtaining a second pH measurement of the bodily sample subsequent to the freezing and thawing cycle.

3. The method of claim 2, wherein said comparing comprises subtracting the second pH measurement from the first pH measurement to obtain a difference value, and wherein said evaluating comprises interpreting a pH difference value of less than 0.2 as an indicator that the female subject has endometriosis and interpreting a pH difference value of greater than 0.2 as an indicator that the female subject does not have endometriosis.

4. The method of claim 3, wherein the bodily sample comprises saliva.

5. The method of claim 1, further comprising:
   collecting the bodily sample and additional bodily samples periodically over at least five consecutive days;
   subjecting the bodily samples to freezing and thawing cycles;
   measuring first pH measurements of the bodily samples prior to the freezing and thawing cycle and obtaining second pH measurements of the bodily samples subsequent to the freezing and thawing cycle;
   for each of the bodily samples, subtracting the second pH measurements from the first pH measurements to obtain difference values; and
   interpreting an occurrence of pH difference values of less than 0.2 for bodily samples collected over five or more consecutive days as an indicator that the female subject has endometriosis, and interpreting a nonoccurrence of more than four pH changes of less than 0.2 for bodily fluid samples collected over five consecutive days as an indicator that the female subject does not have endometriosis.

6. The method of claim 1, wherein said measuring comprises obtaining a first set of optical absorbency measurements of the bodily sample prior to the denaturing procedure and obtaining a second set of optical absorbency measurements of the bodily sample subsequent to the denaturing procedure.

7. A method of screening for endometriosis in a female subject, comprising:
 subjecting a bodily sample to a denaturing procedure, the denaturing procedure comprising dehydrating the bodily sample;
 determining crystalline formations of the dehydrated bodily sample; and
 evaluating the crystalline formations to screen for endometriosis.

8. The method of claim 7, wherein said evaluating comprises:
 obtaining digital micro-photographs of a plurality of dehydrated bodily samples taken over all menstrual cycle phases, the digital microphotographs capturing the crystalline formations of the dehydrated bodily sample; and
 comparing the crystalline formations captured in the digital microphotographs to the reference microphotographs.

9. The method of claim 7, wherein the bodily sample comprises saliva.

10. A method of screening for endometriosis in a female subject, comprising:
 combining a bodily sample with a flavonoid pigment;
 measuring first and second optical density values of the combination of the bodily sample and the flavonoid pigment at first and second wavelengths, respectively, prior to a denaturing procedure;
 subjecting the bodily sample to the denaturing procedure;
 measuring third and fourth optical density values of the combination of the bodily sample and the flavonoid pigment at first and second wavelengths, respectively, subsequent to the denaturing procedure;
 comparing the optical density values prior and subsequent to the denaturing procedure; and
 evaluating said comparison to screen for endometriosis in the female subject.

11. The method of claim 10, wherein the bodily sample comprises saliva.

12. The method of claim 1, further comprising:
 collecting the bodily sample and additional bodily samples periodically over consecutive days;
 subjecting the bodily samples to at least first freezing a thawing cycle and a subsequent second freezing and thawing cycle;
 measuring first pH measurements of the bodily samples after the first freezing and thawing cycle yet before the second freezing and thawing cycle;
 measuring second pH measurements of the bodily samples after the second freezing and thawing cycle;
 for each of the bodily samples, determining differences between the second pH measurements from the first pH measurements to obtain difference values; and
 evaluating variations in the difference values for endometriosis screening of the female subject.

13. The method of claim 12, wherein said evaluating comprises interpreting an occurrence of pH difference values of less than 0.2 for bodily samples collected over five or more consecutive days as an indicator that the female subject has endometriosis, and interpreting a nonoccurrence of more than four pH changes of less than 0.2 for bodily fluid samples collected over five consecutive days as an indicator that the female subject does not have endometriosis.

14. The method of claim 1, further comprising recording the property measured prior and subsequent to the denaturing procedure.

15. The method of claim 7, further comprising recording the crystalline formations.

* * * * *